US010947299B2

(12) United States Patent
Chung et al.

(10) Patent No.: US 10,947,299 B2
(45) Date of Patent: Mar. 16, 2021

(54) ANTIBODY THAT BINDS TO ENVELOPE GLYCOPROTEIN OF SEVERE FEVER WITH THROMBOCYTOPENIA SYNDROME VIRUS AND USE FOR SAME

(71) Applicants: SEOUL NATIONAL UNIVERSITY R&DB FOUNDATION, Seoul (KR); INSTITUT PASTEUR KOREA, Gyeonggi-do (KR)

(72) Inventors: Junho Chung, Gyeonggi-do (KR); Ki-Hyun Kim, Seoul (KR); Hyori Kim, Seoul (KR); Myoung-don Oh, Seoul (KR); Wan Beom Park, Seoul (KR); Seungtaek Kim, Seoul (KR); Jinhee Kim, Gyeonggi-do (KR); Ji-Young Min, Bethesda, MD (US); Meehyun Ko, Gyeonggi-do (KR)

(73) Assignees: SEOUL NATIONAL UNIVERSITY R&DB FOUNDATION, Seoul (KR); INSTITUT PASTEUR KOREA, Gyeonggi-Do (KR)

( * ) Notice: Subject to any disclaimer, the term of this patent is extended or adjusted under 35 U.S.C. 154(b) by 149 days.

(21) Appl. No.: 16/086,761

(22) PCT Filed: Mar. 23, 2017

(86) PCT No.: PCT/KR2017/003156
§ 371 (c)(1),
(2) Date: Sep. 20, 2018

(87) PCT Pub. No.: WO2017/164678
PCT Pub. Date: Sep. 28, 2017

(65) Prior Publication Data
US 2019/0112360 A1    Apr. 18, 2019

(30) Foreign Application Priority Data
Mar. 23, 2016  (KR) .................. 10-2016-0034727

(51) Int. Cl.
C07K 16/10          (2006.01)
C12N 15/62          (2006.01)
(Continued)

(52) U.S. Cl.
CPC .............. *C07K 16/10* (2013.01); *A61K 39/42* (2013.01); *A61P 31/14* (2018.01); *C07K 14/005* (2013.01);
(Continued)

(58) Field of Classification Search
None
See application file for complete search history.

(56) References Cited

U.S. PATENT DOCUMENTS

2011/0091960 A1    4/2011  Siegel
2019/0112360 A1*   4/2019  Chung ................ C07K 14/175

FOREIGN PATENT DOCUMENTS

CN          102942629 A     2/2013
WO       WO-02/051870 A2    7/2002
(Continued)

OTHER PUBLICATIONS

Guo et al. (Clinical and Vaccine Immunology. Sep. 2013; 20 (9): 1426-1432).*
(Continued)

*Primary Examiner* — Shanon A. Foley
(74) *Attorney, Agent, or Firm* — Harness, Dickey & Pierce, P.L.C.

(57) ABSTRACT

The present invention relates to an antibody which specifically binds to the envelope glycoprotein of severe fever with thrombocytopenia syndrome virus (SFTSV), the pathogen of severe fever with thrombocytopenia syndrome (SFTS), and is used in order to effectively detect or diagnosis SFTSV and treat SFTS.

9 Claims, 5 Drawing Sheets

Specification includes a Sequence Listing.

(51) Int. Cl.
```
    A61P 31/14      (2006.01)
    C07K 14/005     (2006.01)
    G01N 33/569     (2006.01)
    G01N 35/00      (2006.01)
    A61K 39/42      (2006.01)
    C07K 14/175     (2006.01)
```
(52) U.S. Cl.
CPC ............ *C07K 14/175* (2013.01); *C12N 15/62* (2013.01); *G01N 33/56983* (2013.01); *G01N 35/00029* (2013.01); *C07K 2317/565* (2013.01); *C07K 2317/622* (2013.01); *C07K 2317/76* (2013.01)

(56) References Cited

FOREIGN PATENT DOCUMENTS

| | | |
|---|---|---|
| WO | WO-03/064606 A2 | 8/2003 |
| WO | WO-2004/006955 A1 | 1/2004 |
| WO | WO-2006/089231 A2 | 8/2006 |
| WO | WO-2010/045388 A2 | 4/2010 |
| WO | WO-2010/059543 A1 | 5/2010 |
| WO | WO-2010/061991 A1 | 6/2010 |
| WO | WO-2010/107752 A2 | 9/2010 |
| WO | WO-2010/141249 A2 | 12/2010 |
| WO | WO-2011/071783 A1 | 6/2011 |
| WO | WO-2012/048340 A2 | 4/2012 |
| WO | WO-2012/076066 A1 | 6/2012 |
| WO | WO-2012/098089 A1 | 7/2012 |
| WO | WO-2012/170438 A2 | 12/2012 |
| WO | WO-2013/063095 A1 | 5/2013 |
| WO | WO-2013/092998 A1 | 6/2013 |
| WO | WO 2015-053455 A1 | 4/2015 |

OTHER PUBLICATIONS

Paul, Fundamental Immunology, 3 rd Edition, 1993, pp. 292-295.*
Rudikoff et al (Proc. Natl. Acad. Sci. USA, 79:1979-1983, Mar. 1982).*
Coleman P. M. (Research in Immunology, 145:33-36, 1994).*
Tani et al. (Virology. 2019; 535: 102-110).*
Li Yu, et al., (2012) "Critical Epitopes in the Nucleocapsid Protein of SFTS Virus Recognized by a Panel of SFTS Patients Derived Human Monoclonal Antibodies.", Jun. 12, 2012, *PloS One, Monoclonal Antibody to SFTSV*, vol. 7, Issue 6, e38291.
Aqian Li Etal: "Preparation and functional analysis of the monoclonal antibodies against severe fever with thrombocytopenia syndrome bunyavirus structural proteins", Chinese Journal of Virology, vol. 31, No. 1, Jan. 1, 2015, pp. 18-23.
Immune Technology Corp: "Anti-G2 (SFTS virus, strain HN6)" Feb. 19, 2013.
Wenshuai Zhang et al: "Computational identification of epitopes in the glycoproteins of novel bunyavirus (SFTS virus) recognized by a human monoclonal antibody (Mab 4-5)" Journal of Computer-Aided Molecular Design., vol. 27, No. 6, Jun. 1, 2013, pp. 539-550.
Guo, et al., "Human Antibody Neutralizes Severe Fever with Thrombocytopenia Syndrome Virus, an Emerging Hemorrhagic Fever Virus.", *Clinical and Vaccine immunology*, (Jul. 17, 2013) (online), vol. 20, No. 9, pp. 1426-1432.
Hofmann, et al., "Severe Fever with Thrombocytopenia Vims Glycoproteins Are Targeted by Neutralizing Antibodies and Can Use DC-SIGN as a Receptor for pH-dependent Entry into Human and Animal Cell Lines.", *Journal of Virology*, (Feb. 6, 2013) (online), vol. 87, No. 8, pp. 4384-4394.
Kim, KH., et al. "Severe fever with thrombocytopenia syndrome, South Korea, 2012.", *Emerging infectious diseases*, (2013) 19(11):1892-4.
Lee, Y. "An antibody reactive to the Gly63-Lys68 epitope of NT-proBNP exhibits O-glycosylation-independent glycosylation-independent binding.", *Experimental & molecular medicine*, (2014) 46:e114.
Liu, et al., "Systematic: Review of Severe Fever with Thrombocytopenia Syndrome: Virology, Epidemiology, and Clinical Characteristics.", *Reviews in Medical Virology*, Dec. 6, 2013 (online), vol. 24, pp. 90-102.
Park, S., et al. "A sensitive enzyme immunoassay for measuring cotinine in passive smokers.", *Clinica chimica acta; international journal of clinical chemistry*, (2010) 411(17-18):1238-42. (Abstract only).
International Search Report from corresponding International Patent Application No. PCT/KR2017/003156 , dated Jun. 26, 2017, with an English translation.
Extended European Search Report from corresponding European Patent Application No. 17770648.8, dated Feb. 28, 2020.
D.X. Li et al., "Severe fever with thrombocytopenia syndrome: a newly discovered emerging infectious disease", Clinicalmicrobiologyand Infection.; vol. 21, No. 7, Jul. 1, 2015, pp. 614-620.
Eenzyme,"Accelerating Scientific Discovery Membrane Glycoprotein G2 of Phlebovirus (SFTS virus HN6)", Apr. 14, 2009, XP055625219, retrieved on Sep. 23, 2019.
Satoshi Shimada et al., "Therapeutic effect of post-exposure treatment with antiserum on severe fever with thrombocytopenia syndrome (SFTS) in a mouse model of SFTS virus infection", Virology, vol. 482, Mar. 26, 2015, pp. 19-27.

\* cited by examiner

SEQUENCE LISTING

```
<160> NUMBER OF SEQ ID NOS: 171

<210> SEQ ID NO 1
<211> LENGTH: 108
<212> TYPE: PRT
<213> ORGANISM: Artificial Sequence
<220> FEATURE:
<223> OTHER INFORMATION: Ab1 Light chain

<400> SEQUENCE: 1

Glu Leu Thr Leu Thr Gln Ser Pro Ala Thr Leu Ser Leu Ser Pro Gly
1               5                   10                  15

Glu Thr Ala Thr Leu Ser Cys Gly Ala Ser Gln Ser Val Ser Thr Asn
            20                  25                  30

Tyr Leu Ala Trp Tyr Gln Gln Lys Pro Gly Leu Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Ala
65                  70                  75                  80

Pro Glu Asp Ser Ala Val Tyr Tyr Cys Gln Gln Tyr Gly Ser Ser Pro
                85                  90                  95

Leu Thr Phe Gly Gly Gly Thr Lys Leu Glu Ile Lys
            100                 105

<210> SEQ ID NO 2
<211> LENGTH: 110
<212> TYPE: PRT
<213> ORGANISM: Artificial Sequence
<220> FEATURE:
<223> OTHER INFORMATION: Ab2 Light chain

<400> SEQUENCE: 2

Glu Leu Val Val Thr Gln Pro Pro Ser Val Ser Gly Ala Pro Gly Gln
1               5                   10                  15

Arg Val Thr Ile Ser Cys Ser Gly Ser Ser Ser Asn Ile Gly Asn Asn
            20                  25                  30
```

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Thr Gly Leu Gln
 65                  70                  75                  80

Ala Asp Asp Glu Ala Asp Tyr Tyr Cys Gln Ser Phe Asp Ser Ser Leu
                85                  90                  95

Asn Asp Trp Val Phe Gly Gly Gly Thr Lys Leu Thr Val Leu
            100                 105                 110

<210> SEQ ID NO 3
<211> LENGTH: 112
<212> TYPE: PRT
<213> ORGANISM: Artificial Sequence
<220> FEATURE:
<223> OTHER INFORMATION: Ab3 Light chain

<400> SEQUENCE: 3

Glu Leu Glu Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
 50                  55                  60

Ser Gly Ser Lys Ser Asp Thr Ser Ala Ser Leu Ala Ile Ser Gly Leu
 65                  70                  75                  80

Arg Ser Glu Asp Glu Ala Asp Tyr Tyr Cys Ala Ala Trp Asp Asp Ser
                85                  90                  95

Leu Asn Gly Gln Val Val Phe Gly Gly Gly Thr Lys Leu Thr Val Leu
            100                 105                 110

<210> SEQ ID NO 4
<211> LENGTH: 109
<212> TYPE: PRT
<213> ORGANISM: Artificial Sequence
<220> FEATURE:
<223> OTHER INFORMATION: Ab4 Light chain

<400> SEQUENCE: 4

Glu Leu Val Leu Thr Gln Pro Pro Ser Ala Ser Gly Thr Pro Gly Gln
 1               5                  10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Pro Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Gln Ser Tyr Asp Ser Ser Leu
                85                  90                  95

Ser Tyr Val Phe Gly Thr Gly Thr Lys Val Thr Val Leu
            100                 105

<210> SEQ ID NO 5

<211> LENGTH: 109
<212> TYPE: PRT
<213> ORGANISM: Artificial Sequence
<220> FEATURE:
<223> OTHER INFORMATION: Ab5 Light chain

<400> SEQUENCE: 5

```
Glu Leu Val Val Thr Gln Glu Pro Ser Leu Thr Val Pro Pro Gly Gly
1               5                   10                  15

Thr Val Thr Leu Thr Cys Gly Ser Ser Thr Gly Pro Val Thr Thr Thr
            20                  25                  30

Gln Tyr Pro Tyr Trp Phe Gln Gln Lys Pro Gly Gln Ala Pro Arg Thr
        35                  40                  45

Leu Ile Tyr Asp Thr Asn Asn Arg His Pro Trp Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Asp Ala Tyr Tyr Cys Leu Leu Thr Ser Ala Ser Ala
                85                  90                  95

Pro Trp Val Phe Gly Gly Gly Thr Lys Leu Thr Val Leu
            100                 105
```

<210> SEQ ID NO 6
<211> LENGTH: 121
<212> TYPE: PRT
<213> ORGANISM: Artificial Sequence
<220> FEATURE:
<223> OTHER INFORMATION: Ab1 Heavy chain

<400> SEQUENCE: 6

```
Gln Val Gln Leu Val Gln Ser Gly Pro Glu Val Lys Lys Pro Gly Ser
1               5                   10                  15

Ser Val Lys Val Ser Cys Lys Ala Ser Gly Gly Thr Phe Ser Thr Tyr
            20                  25                  30

Ala Ile Ser Trp Val Arg Gln Ala Pro Gly Gln Gly Leu Glu Trp Met
        35                  40                  45

Gly Gly Ile Ile Pro Ile Ser Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Val Pro Val Val Pro Ala Ala Ser Gly Pro Phe Asp Tyr Trp Gly
            100                 105                 110

Gln Gly Thr Leu Val Thr Val Ser Ser
        115                 120
```

<210> SEQ ID NO 7
<211> LENGTH: 130
<212> TYPE: PRT
<213> ORGANISM: Artificial Sequence
<220> FEATURE:
<223> OTHER INFORMATION: Ab2 Heavy chain

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Asn Trp Val Arg Gln Ala Pro Gly Lys Gly Leu Glu Trp Val
            35                  40                  45

Ser Ser Ile Ser Ser Ser Ser Arg Tyr Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Ser Leu Gly Tyr Cys Ser Gly Ser Cys Tyr Gly Phe Pro Glu
            100                 105                 110

Gly Gly Asn Ala Phe Asp Ile Trp Gly Gln Gly Thr Met Val Thr Val
            115                 120                 125

Ser Ser
    130
```

<210> SEQ ID NO 8
<211> LENGTH: 120
<212> TYPE: PRT
<213> ORGANISM: Artificial Sequence
<220> FEATURE:
<223> OTHER INFORMATION: Ab3 Heavy chain

<400> SEQUENCE: 8

```
Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Ile His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Gly Asp Tyr Tyr Asp Ser Ser Gly Ala Phe Asp Tyr Trp Gly Gln
            100                 105                 110

Gly Thr Leu Val Thr Val Ser Ser
            115                 120
```

<210> SEQ ID NO 9
<211> LENGTH: 128
<212> TYPE: PRT
<213> ORGANISM: Artificial Sequence
<220> FEATURE:
<223> OTHER INFORMATION: Ab4 Heavy chain

<400> SEQUENCE: 9

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Ser Ile Ser Ser Ser Ser Arg Tyr Ile Phe Tyr Ala Asp Ser Val
        50                  55                  60

Lys Gly Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Ser
                85                  90                  95

Leu Gly Tyr Cys Ser Gly Gly Ser Cys Tyr Gly Phe Pro Glu Gly Gly
            100                 105                 110

Asn Ala Phe Asp Ile Trp Gly Gln Gly Thr Met Val Thr Val Ser Ser
        115                 120                 125

<210> SEQ ID NO 10
<211> LENGTH: 118
<212> TYPE: PRT
<213> ORGANISM: Artificial Sequence
<220> FEATURE:
<223> OTHER INFORMATION: Ab5 Heavy chain

<400> SEQUENCE: 10

Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Asn Asp Gly Ser Ser Asn His Phe Asp Tyr Trp Gly Gln Gly Thr
            100                 105                 110

Leu Val Thr Val Ser Ser
        115

<210> SEQ ID NO 11
<211> LENGTH: 23
<212> TYPE: PRT
<213> ORGANISM: Artificial Sequence
<220> FEATURE:
<223> OTHER INFORMATION: Ab1 LFR1

<400> SEQUENCE: 11

Glu Leu Thr Leu Thr Gln Ser Pro Ala Thr Leu Ser Leu Ser Pro Gly
1               5                   10                  15

Glu Thr Ala Thr Leu Ser Cys
            20

<210> SEQ ID NO 12
<211> LENGTH: 22
<212> TYPE: PRT
<213> ORGANISM: Artificial Sequence
<220> FEATURE:
<223> OTHER INFORMATION: Ab2 LFR1

<400> SEQUENCE: 12

Glu Leu Val Val Thr Gln Pro Pro Ser Val Ser Gly Ala Pro Gly Gln
1               5                   10                  15

Arg Val Thr Ile Ser Cys
            20

<210> SEQ ID NO 13
<211> LENGTH: 22

```
<212> TYPE: PRT
<213> ORGANISM: Artificial Sequence
<220> FEATURE:
<223> OTHER INFORMATION: Ab3 LFR1

<400> SEQUENCE: 13

Glu Leu Glu Leu Thr Gln Pro Pro Ser Val Ser Gly Ala Pro Gly Gln
1               5                   10                  15

Arg Val Thr Ile Ser Cys
            20

<210> SEQ ID NO 14
<211> LENGTH: 22
<212> TYPE: PRT
<213> ORGANISM: Artificial Sequence
<220> FEATURE:
<223> OTHER INFORMATION: Ab4 LFR1

<400> SEQUENCE: 14

Glu Leu Val Leu Thr Gln Pro Pro Ser Ala Ser Gly Thr Pro Gly Gln
1               5                   10                  15

Arg Val Thr Ile Ser Cys
            20

<210> SEQ ID NO 15
<211> LENGTH: 22
<212> TYPE: PRT
<213> ORGANISM: Artificial Sequence
<220> FEATURE:
<223> OTHER INFORMATION: Ab5 LFR1

<400> SEQUENCE: 15

Glu Leu Val Val Thr Gln Glu Pro Ser Leu Thr Val Pro Pro Gly Gly
1               5                   10                  15

Thr Val Thr Leu Thr Cys
            20

<210> SEQ ID NO 16
<211> LENGTH: 25
<212> TYPE: PRT
<213> ORGANISM: Artificial Sequence
<220> FEATURE:
<223> OTHER INFORMATION: Ab1 HFR1

<400> SEQUENCE: 16

Gln Val Gln Leu Val Gln Ser Gly Pro Glu Val Lys Lys Pro Gly Ser
1               5                   10                  15

Ser Val Lys Val Ser Cys Lys Ala Ser
            20                  25

<210> SEQ ID NO 17
<211> LENGTH: 25
<212> TYPE: PRT
<213> ORGANISM: Artificial Sequence
<220> FEATURE:
<223> OTHER INFORMATION: Ab2 HFR1

<400> SEQUENCE: 17

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 18
```

<211> LENGTH: 25
<212> TYPE: PRT
<213> ORGANISM: Artificial Sequence
<220> FEATURE:
<223> OTHER INFORMATION: Ab3 HFR1

<400> SEQUENCE: 18

Gln Val Gln Leu Gln Glu Ser Gly Pro Gly Leu Val Lys Pro Ser Glu
1               5                   10                  15

Thr Leu Ser Leu Thr Cys Thr Val Ser
            20                  25

<210> SEQ ID NO 19
<211> LENGTH: 25
<212> TYPE: PRT
<213> ORGANISM: Artificial Sequence
<220> FEATURE:
<223> OTHER INFORMATION: Ab4 HFR1

<400> SEQUENCE: 19

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 20
<211> LENGTH: 25
<212> TYPE: PRT
<213> ORGANISM: Artificial Sequence
<220> FEATURE:
<223> OTHER INFORMATION: Ab5 HFR1

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 21
<211> LENGTH: 12
<212> TYPE: PRT
<213> ORGANISM: Artificial Sequence
<220> FEATURE:
<223> OTHER INFORMATION: Ab1 LCDR1

<400> SEQUENCE: 21

Gly Ala Ser Gln Ser Val Ser Thr Asn Tyr Leu Ala
1               5                   10

<210> SEQ ID NO 22
<211> LENGTH: 13
<212> TYPE: PRT
<213> ORGANISM: Artificial Sequence
<220> FEATURE:
<223> OTHER INFORMATION: Ab2 LCDR1

<400> SEQUENCE: 22

Ser Gly Ser Ser Ser Asn Ile Gly Asn Asn Thr Val Asn
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Ab3 LCDR1

-continued

<400> SEQUENCE: 23

Thr Gly Ser Ser Ser Asn Ile Gly Ala Gly Tyr Asp Val His
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Ab4 LCDR1

<400> SEQUENCE: 24

Ser Gly Ser Ser Ser Asn Ile Gly Ser Asn Thr Val Asn
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Ab5 LCDR1

<400> SEQUENCE: 25

Gly Ser Ser Thr Gly Pro Val Thr Thr Thr Gln Tyr Pro Tyr
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Ab1 HCDR1

<400> SEQUENCE: 26

Gly Gly Thr Phe Ser Thr Tyr Ala Ile Ser
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Ab2 HCDR1

<400> SEQUENCE: 27

Gly Phe Thr Phe Ser Ser Tyr Ser Met Asn
1               5                   10

<210> SEQ ID NO 28
<211> LENGTH: 10
<212> TYPE: PRT
<213> ORGANISM: Artificial Sequence
<220> FEATURE:
<223> OTHER INFORMATION: Ab3 HCDR1

<400> SEQUENCE: 28

Gly Gly Ser Phe Ser Gly Tyr Tyr Trp Ser
1               5                   10

<210> SEQ ID NO 29
<211> LENGTH: 10
<212> TYPE: PRT
<213> ORGANISM: Artificial Sequence
<220> FEATURE:
<223> OTHER INFORMATION: Ab4 HCDR1

<400> SEQUENCE: 29

Gly Phe Thr Phe Ser Ser Tyr Ser Met Asn
1               5                   10

<210> SEQ ID NO 30
<211> LENGTH: 10
<212> TYPE: PRT
<213> ORGANISM: Artificial Sequence
<220> FEATURE:
<223> OTHER INFORMATION: Ab5 HCDR1

<400> SEQUENCE: 30

Gly Phe Thr Phe Ser Ser Tyr Ala Met His
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Ab1 LFR2

<400> SEQUENCE: 31

Trp Tyr Gln Gln Lys Pro Gly Leu Ala Pro Arg Leu Leu Ile Tyr
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Ab2 LFR2

<400> SEQUENCE: 32

Trp Tyr Gln Gln Leu Pro Gly Thr Ala Pro Lys Leu Leu Ile Tyr
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Ab3 LFR2

<400> SEQUENCE: 33

Trp Tyr Gln Gln Leu Pro Gly Thr Ala Pro Lys Leu Leu Ile Tyr
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Ab4 LFR2

<400> SEQUENCE: 34

Trp Tyr Gln Gln Leu Pro Gly Thr Ala Pro Lys Leu Leu Ile Tyr
1               5                   10                  15

<210> SEQ ID NO 35
<211> LENGTH: 15
<212> TYPE: PRT
<213> ORGANISM: Artificial Sequence
<220> FEATURE:
<223> OTHER INFORMATION: Ab5 LFR2

<400> SEQUENCE: 35

Trp Phe Gln Gln Lys Pro Gly Gln Ala Pro Arg Thr Leu Ile Tyr
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: Ab1 HFR2

<400> SEQUENCE: 36

Trp Val Arg Gln Ala Pro Gly Gln Gly Leu Glu Trp Met Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: Ab2 HFR2

<400> SEQUENCE: 37

Trp Val Arg Gln Ala Pro Gly Lys Gly Leu Glu Trp Val Ser
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Ab3 HFR2

<400> SEQUENCE: 38

Trp Ile Arg Gln Pro Pro Gly Lys Gly Leu Glu Trp Ile Gly
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Ab4 HFR2

<400> SEQUENCE: 39

Trp Val Arg Gln Ala Pro Gly Lys Gly Leu Glu Trp Val Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Ab5 HFR2

<400> SEQUENCE: 40

Trp Val Arg Gln Ala Pro Gly Lys Gly Leu Glu Tyr Val Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: Ab1 LCDR2

<400> SEQUENCE: 41

```
Asp Ala Ser Ser Arg Ala Thr
1               5

<210> SEQ ID NO 42
<211> LENGTH: 7
<212> TYPE: PRT
<213> ORGANISM: Artificial Sequence
<220> FEATURE:
<223> OTHER INFORMATION: Ab2 LCDR2

<400> SEQUENCE: 42

Ser Asn Asn Gln Arg Pro Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Ab3 LCDR2

<400> SEQUENCE: 43

Gly Asn Ser Asn Arg Pro Ser
1               5

<210> SEQ ID NO 44
<211> LENGTH: 7
<212> TYPE: PRT
<213> ORGANISM: Artificial Sequence
<220> FEATURE:
<223> OTHER INFORMATION: Ab4 LCDR2

<400> SEQUENCE: 44

Ser Asn Asn Gln Arg Pro Pro
1               5

<210> SEQ ID NO 45
<211> LENGTH: 7
<212> TYPE: PRT
<213> ORGANISM: Artificial Sequence
<220> FEATURE:
<223> OTHER INFORMATION: Ab5 LCDR2

<400> SEQUENCE: 45

Asp Thr Asn Asn Arg His Pro
1               5

<210> SEQ ID NO 46
<211> LENGTH: 17
<212> TYPE: PRT
<213> ORGANISM: Artificial Sequence
<220> FEATURE:
<223> OTHER INFORMATION: Ab1 HCDR2

<400> SEQUENCE: 46

Gly Ile Ile Pro Ile Ser Gly Thr Ala Asn Tyr Ala Gln Lys Phe Gln
1               5                   10                  15

Gly

<210> SEQ ID NO 47
<211> LENGTH: 17
<212> TYPE: PRT
<213> ORGANISM: Artificial Sequence
<220> FEATURE:
<223> OTHER INFORMATION: Ab2 HCDR2

<400> SEQUENCE: 47
```

```
Ser Ile Ser Ser Ser Ser Arg Tyr Ile Phe Tyr Ala Asp Ser Val Lys
1               5                   10                  15

Gly

<210> SEQ ID NO 48
<211> LENGTH: 16
<212> TYPE: PRT
<213> ORGANISM: Artificial Sequence
<220> FEATURE:
<223> OTHER INFORMATION: Ab3 HCDR2

<400> SEQUENCE: 48

Glu Ile Ile His Ser Gly Ser Thr Asn Tyr Asn Pro Ser Leu Lys Ser
1               5                   10                  15

<210> SEQ ID NO 49
<211> LENGTH: 17
<212> TYPE: PRT
<213> ORGANISM: Artificial Sequence
<220> FEATURE:
<223> OTHER INFORMATION: Ab4 HCDR2

<400> SEQUENCE: 49

Ser Ile Ser Ser Ser Ser Arg Tyr Ile Phe Tyr Ala Asp Ser Val Lys
1               5                   10                  15

Gly

<210> SEQ ID NO 50
<211> LENGTH: 17
<212> TYPE: PRT
<213> ORGANISM: Artificial Sequence
<220> FEATURE:
<223> OTHER INFORMATION: Ab5 HCDR2

<400> SEQUENCE: 50

Ala Ile Ser Ser Asp Gly Gly Ser Thr Tyr Tyr Ala Asp Ser Val Lys
1               5                   10                  15

Gly

<210> SEQ ID NO 51
<211> LENGTH: 32
<212> TYPE: PRT
<213> ORGANISM: Artificial Sequence
<220> FEATURE:
<223> OTHER INFORMATION: Ab1 LFR3

<400> SEQUENCE: 51

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Ab2 LFR3

<400> SEQUENCE: 52

Gly Val Pro Asp Arg Phe Ser Gly Ser Lys Ser Gly Thr Ser Ala Ser
1               5                   10                  15

Leu Ala Ile Ser Gly Leu Gln Ser Glu Asp Glu Ala Asp Tyr Tyr Cys
```

<210> SEQ ID NO 53
<211> LENGTH: 32
<212> TYPE: PRT
<213> ORGANISM: Artificial Sequence
<220> FEATURE:
<223> OTHER INFORMATION: Ab3 LFR3

<400> SEQUENCE: 53

Gly Val Pro Asp Arg Phe Ser Gly Ser Lys Ser Asp Thr Ser Ala Ser
1               5                   10                  15
Leu Ala Ile Ser Gly Leu Arg Ser Glu Asp Glu Ala Asp Tyr Tyr Cys
                20                  25                  30

<210> SEQ ID NO 54
<211> LENGTH: 32
<212> TYPE: PRT
<213> ORGANISM: Artificial Sequence
<220> FEATURE:
<223> OTHER INFORMATION: Ab4 LFR3

<400> SEQUENCE: 54

Gly Val Pro Asp Arg Phe Ser Gly Ser Lys Ser Gly Thr Ser Ala Ser
1               5                   10                  15
Leu Ala Ile Ser Gly Leu Gln Ser Glu Asp Glu Ala Asp Tyr Tyr Cys
                20                  25                  30

<210> SEQ ID NO 55
<211> LENGTH: 31
<212> TYPE: PRT
<213> ORGANISM: Artificial Sequence
<220> FEATURE:
<223> OTHER INFORMATION: Ab5 LFR3

<400> SEQUENCE: 55

Trp Thr Pro Ala Arg Phe Ser Gly Ser Leu Leu Gly Gly Lys Ala Ala
1               5                   10                  15
Leu Thr Leu Ser Gly Ala Gln Pro Glu Asp Asp Ala Tyr Tyr Cys
                20                  25                  30

<210> SEQ ID NO 56
<211> LENGTH: 31
<212> TYPE: PRT
<213> ORGANISM: Artificial Sequence
<220> FEATURE:
<223> OTHER INFORMATION: Ab1 HFR3

<400> SEQUENCE: 56

Arg Val Thr Ile Thr Ala Asp Glu Ser Thr Ser Thr Ala Tyr Met Glu
1               5                   10                  15
Leu Ser Ser Leu Arg Ser Glu Asp Thr Ala Val Tyr Tyr Cys Ala
                20                  25                  30

<210> SEQ ID NO 57
<211> LENGTH: 31
<212> TYPE: PRT
<213> ORGANISM: Artificial Sequence
<220> FEATURE:
<223> OTHER INFORMATION: Ab2 HFR3

<400> SEQUENCE: 57

Arg Phe Thr Ile Ser Arg Asp Asn Ala Lys Asn Ser Leu Tyr Leu Gln
1               5                   10                  15

```
Met Asn Ser Leu Arg Ala Glu Asp Thr Ala Val Tyr Tyr Cys Ala
            20                  25                  30
```

<210> SEQ ID NO 58
<211> LENGTH: 31
<212> TYPE: PRT
<213> ORGANISM: Artificial Sequence
<220> FEATURE:
<223> OTHER INFORMATION: Ab3 HFR3

<400> SEQUENCE: 58

```
Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30
```

<210> SEQ ID NO 59
<211> LENGTH: 29
<212> TYPE: PRT
<213> ORGANISM: Artificial Sequence
<220> FEATURE:
<223> OTHER INFORMATION: Ab4 HFR3

<400> SEQUENCE: 59

```
Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr
            20                  25
```

<210> SEQ ID NO 60
<211> LENGTH: 31
<212> TYPE: PRT
<213> ORGANISM: Artificial Sequence
<220> FEATURE:
<223> OTHER INFORMATION: Ab5 HFR3

<400> SEQUENCE: 60

```
Arg Phe Thr Ile Ser Arg Asp Asn Ser Lys Asn Thr Leu Tyr Leu Gln
1               5                   10                  15

Met Ser Ser Leu Arg Ala Glu Asp Thr Ala Val Tyr Tyr Cys Val
            20                  25                  30
```

<210> SEQ ID NO 61
<211> LENGTH: 9
<212> TYPE: PRT
<213> ORGANISM: Artificial Sequence
<220> FEATURE:
<223> OTHER INFORMATION: Ab1 LCDR3

<400> SEQUENCE: 61

```
Gln Gln Tyr Gly Ser Ser Pro Leu Thr
1               5
```

<210> SEQ ID NO 62
<211> LENGTH: 11
<212> TYPE: PRT
<213> ORGANISM: Artificial Sequence
<220> FEATURE:
<223> OTHER INFORMATION: Ab2 LCDR3

<400> SEQUENCE: 62

```
Gln Ser Phe Asp Ser Ser Leu Asn Asp Trp Val
1               5                   10
```

<210> SEQ ID NO 63

```
<211> LENGTH: 12
<212> TYPE: PRT
<213> ORGANISM: Artificial Sequence
<220> FEATURE:
<223> OTHER INFORMATION: Ab3 LCDR3

<400> SEQUENCE: 63

Ala Ala Trp Asp Asp Ser Leu Asn Gly Gln Val Val
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Ab4 LCDR3

<400> SEQUENCE: 64

Gln Ser Tyr Asp Ser Ser Leu Ser Tyr Val
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Ab5 LCDR3

<400> SEQUENCE: 65

Leu Leu Thr Ser Ala Ser Ala Pro Trp Val
1               5                   10

<210> SEQ ID NO 66
<211> LENGTH: 15
<212> TYPE: PRT
<213> ORGANISM: Artificial Sequence
<220> FEATURE:
<223> OTHER INFORMATION: Ab1 HCDR3

<400> SEQUENCE: 66

Val Pro Val Val Pro Ala Ala Ser Gly Pro Phe Asp Tyr Trp Gly
1               5                   10                  15

<210> SEQ ID NO 67
<211> LENGTH: 24
<212> TYPE: PRT
<213> ORGANISM: Artificial Sequence
<220> FEATURE:
<223> OTHER INFORMATION: Ab2 HCDR3

<400> SEQUENCE: 67

Ser Leu Gly Tyr Cys Ser Gly Gly Ser Cys Tyr Gly Phe Pro Glu Gly
1               5                   10                  15

Gly Asn Ala Phe Asp Ile Trp Gly
            20

<210> SEQ ID NO 68
<211> LENGTH: 15
<212> TYPE: PRT
<213> ORGANISM: Artificial Sequence
<220> FEATURE:
<223> OTHER INFORMATION: Ab3 HCDR3

<400> SEQUENCE: 68

Arg Gly Asp Tyr Tyr Asp Ser Ser Gly Ala Phe Asp Tyr Trp Gly
1               5                   10                  15
```

<210> SEQ ID NO 69
<211> LENGTH: 24
<212> TYPE: PRT
<213> ORGANISM: Artificial Sequence
<220> FEATURE:
<223> OTHER INFORMATION: Ab4 HCDR3

<400> SEQUENCE: 69

Ser Leu Gly Tyr Cys Ser Gly Gly Ser Cys Tyr Gly Phe Pro Glu Gly
1               5                   10                  15

Gly Asn Ala Phe Asp Ile Trp Gly
            20

<210> SEQ ID NO 70
<211> LENGTH: 12
<212> TYPE: PRT
<213> ORGANISM: Artificial Sequence
<220> FEATURE:
<223> OTHER INFORMATION: Ab5 HCDR3

<400> SEQUENCE: 70

Asn Asp Gly Ser Ser Asn His Phe Asp Tyr Trp Gly
1               5                   10

<210> SEQ ID NO 71
<211> LENGTH: 10
<212> TYPE: PRT
<213> ORGANISM: Artificial Sequence
<220> FEATURE:
<223> OTHER INFORMATION: Ab1 LFR4

<400> SEQUENCE: 71

Phe Gly Gly Gly Thr Lys Leu Glu Ile Lys
1               5                   10

<210> SEQ ID NO 72
<211> LENGTH: 10
<212> TYPE: PRT
<213> ORGANISM: Artificial Sequence
<220> FEATURE:
<223> OTHER INFORMATION: Ab2 LFR4

<400> SEQUENCE: 72

Phe Gly Gly Gly Thr Lys Leu Thr Val Leu
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Ab3 LFR4

<400> SEQUENCE: 73

Phe Gly Gly Gly Thr Lys Leu Thr Val Leu
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Ab4 LFR4

<400> SEQUENCE: 74

Phe Gly Thr Gly Thr Lys Val Thr Val Leu

```
1               5                  10
```

<210> SEQ ID NO 75
<211> LENGTH: 10
<212> TYPE: PRT
<213> ORGANISM: Artificial Sequence
<220> FEATURE:
<223> OTHER INFORMATION: Ab5 LFR4

<400> SEQUENCE: 75

```
Phe Gly Gly Gly Thr Lys Leu Thr Val Leu
1               5                  10
```

<210> SEQ ID NO 76
<211> LENGTH: 9
<212> TYPE: PRT
<213> ORGANISM: Artificial Sequence
<220> FEATURE:
<223> OTHER INFORMATION: Ab1 HFR4

<400> SEQUENCE: 76

```
Gln Gly Thr Leu Val Thr Val Ser Ser
1               5
```

<210> SEQ ID NO 77
<211> LENGTH: 9
<212> TYPE: PRT
<213> ORGANISM: Artificial Sequence
<220> FEATURE:
<223> OTHER INFORMATION: Ab2 HFR4

<400> SEQUENCE: 77

```
Gln Gly Thr Met Val Thr Val Ser Ser
1               5
```

<210> SEQ ID NO 78
<211> LENGTH: 9
<212> TYPE: PRT
<213> ORGANISM: Artificial Sequence
<220> FEATURE:
<223> OTHER INFORMATION: Ab3 HFR4

<400> SEQUENCE: 78

```
Gln Gly Thr Leu Val Thr Val Ser Ser
1               5
```

<210> SEQ ID NO 79
<211> LENGTH: 9
<212> TYPE: PRT
<213> ORGANISM: Artificial Sequence
<220> FEATURE:
<223> OTHER INFORMATION: Ab4 HFR4

<400> SEQUENCE: 79

```
Gln Gly Thr Met Val Thr Val Ser Ser
1               5
```

<210> SEQ ID NO 80
<211> LENGTH: 9
<212> TYPE: PRT
<213> ORGANISM: Artificial Sequence
<220> FEATURE:
<223> OTHER INFORMATION: Ab5 HFR4

<400> SEQUENCE: 80

```
Gln Gly Thr Leu Val Thr Val Ser Ser
1               5
```

<210> SEQ ID NO 81
<211> LENGTH: 108
<212> TYPE: PRT
<213> ORGANISM: Artificial Sequence
<220> FEATURE:
<223> OTHER INFORMATION: Ab6 Light chain

<400> SEQUENCE: 81

```
Glu Leu Ala Leu Thr Gln Pro Pro Ser Val Ser Val Ala Pro Gly Lys
1               5                   10                  15

Thr Ala Lys Ile Thr Cys Gly Gly Asp Asp Ile Gly Ser Lys Thr Val
            20                  25                  30

Gln Trp Tyr Gln Gln Thr Ser Gly Gln Ala Pro Val Leu Val Val Tyr
        35                  40                  45

Asp Asp Ser Asp Arg Pro Ser Gly Ile Pro Glu Arg Phe Ser Gly Ala
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Arg Ser Asp His
                85                  90                  95

Val Val Phe Gly Gly Gly Thr Lys Leu Thr Val Leu
            100                 105
```

<210> SEQ ID NO 82
<211> LENGTH: 112
<212> TYPE: PRT
<213> ORGANISM: Artificial Sequence
<220> FEATURE:
<223> OTHER INFORMATION: Ab7 Light chain

<400> SEQUENCE: 82

```
Glu Leu Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Val Val Ser Trp Tyr Gln Gln Leu Pro Gly Thr Ala Pro Lys Leu Leu
        35                  40                  45

Ile Tyr Asp Asp Asn Arg Arg Pro Ser Gly Ile Pro Asp Arg Phe Ser
    50                  55                  60

Gly Ser Lys Ser Gly Thr Ser Ala Thr Leu Asp Ile Thr Gly Leu Gln
65                  70                  75                  80

Thr Gly Asp Glu Ala Asp Tyr Tyr Cys Ala Thr Trp Asp Gly Ser Leu
                85                  90                  95

Thr Ala Gly Arg Val Leu Phe Gly Ser Gly Thr Lys Leu Thr Val Leu
            100                 105                 110
```

<210> SEQ ID NO 83
<211> LENGTH: 108
<212> TYPE: PRT
<213> ORGANISM: Artificial Sequence
<220> FEATURE:
<223> OTHER INFORMATION: Ab8 Light chain

<400> SEQUENCE: 83

```
Glu Leu Ala Leu Thr Gln Pro Pro Ser Val Ser Val Ala Pro Ala Met
1               5                   10                  15

Thr Ala Lys Ile Thr Cys Gly Gly Asp Asp Ile Gly Ser Thr Thr Val
            20                  25                  30
```

```
Gln Trp Tyr Gln Gln Thr Ser Gly Gln Ala Pro Val Leu Val Tyr
         35                  40                  45

Asp Asp Ser Asp Arg Pro Ser Gly Ile Pro Glu Arg Phe Ser Gly Ala
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Gly Arg Ser Asp His
                 85                  90                  95

Val Val Phe Gly Gly Gly Thr Lys Leu Thr Val Leu
            100                 105

<210> SEQ ID NO 84
<211> LENGTH: 110
<212> TYPE: PRT
<213> ORGANISM: Artificial Sequence
<220> FEATURE:
<223> OTHER INFORMATION: Ab9 Light chain

<400> SEQUENCE: 84

Glu Leu Glu Leu Thr Gln Pro Pro Ser Val Ser Gly Thr Pro Gly Lys
 1               5                  10                  15

Arg Val Ser Met Ser Cys Ser Gly Ser Arg Ser Asn Ile Gly Gly Asn
             20                  25                  30

Val Val Asn Trp Tyr Gln Gln Leu Pro Gly Lys Ala Pro Lys Leu Phe
         35                  40                  45

Ile Tyr Asn Asn Asp Gln Arg Pro Ser Gly Val Pro Asp Arg Val Ser
 50                  55                  60

Gly Ser Lys Ser Gly Thr Ser Val Ser Val Ala Ile Ser Gly Leu Gln
 65                  70                  75                  80

Pro Glu Asp Glu Ala Asp Tyr Tyr Cys Ala Ala Trp Asp Asp Ile Leu
                 85                  90                  95

Asn Gly Val Val Phe Gly Gly Gly Thr Gln Leu Thr Val Leu
            100                 105                 110

<210> SEQ ID NO 85
<211> LENGTH: 107
<212> TYPE: PRT
<213> ORGANISM: Artificial Sequence
<220> FEATURE:
<223> OTHER INFORMATION: Ab10 Light chain

<400> SEQUENCE: 85

Glu Leu Val Met Thr Gln Ser Pro Ser Ser Leu Ser Ala Ser Val Gly
 1               5                  10                  15

Asp Thr Val Thr Ile Thr Cys Arg Ala Ser Gln Ser Ile Tyr Thr Tyr
             20                  25                  30

Leu Asn Trp Tyr His Gln Thr Pro Gly Lys Ala Pro Lys Leu Leu Ile
         35                  40                  45

Ser Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ala Asp Val Pro Val
                 85                  90                  95

Thr Phe Gly Gly Gly Thr Lys Leu Glu Ile Lys
            100                 105

<210> SEQ ID NO 86
```

<211> LENGTH: 128
<212> TYPE: PRT
<213> ORGANISM: Artificial Sequence
<220> FEATURE:
<223> OTHER INFORMATION: Ab6 Heavy chain

<400> SEQUENCE: 86

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Lys Leu Arg Gly Phe Ser Gly Tyr Gly Ser Gly Arg
            100                 105                 110

Arg Tyr Phe Asp Tyr Trp Gly Gln Gly Thr Leu Val Thr Val Ser Ser
            115                 120                 125

<210> SEQ ID NO 87
<211> LENGTH: 128
<212> TYPE: PRT
<213> ORGANISM: Artificial Sequence
<220> FEATURE:
<223> OTHER INFORMATION: Ab7 Heavy chain

<400> SEQUENCE: 87

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Lys Leu Arg Gly Phe Ser Gly Gly Tyr Gly Ser Gly Ser
            100                 105                 110

Arg Tyr Phe Asp Tyr Trp Gly Gln Gly Thr Leu Val Thr Val Ser Ser
            115                 120                 125

<210> SEQ ID NO 88
<211> LENGTH: 128
<212> TYPE: PRT
<213> ORGANISM: Artificial Sequence
<220> FEATURE:
<223> OTHER INFORMATION: Ab8 Heavy chain

<400> SEQUENCE: 88

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Arg Ser Ile Ser Thr Ala Asn
65                  70                  75                  80

Leu Gln Trp Ser Ser Leu Lys Ala Ser Asp Thr Ala Leu Tyr Tyr Cys
                85                  90                  95

Ala Arg Leu Lys Leu Arg Gly Phe Ser Gly Tyr Gly Ser Gly Arg
            100                 105                 110

Arg Tyr Phe Asp Tyr Trp Gly Gln Gly Thr Leu Val Thr Val Ser Ser
            115                 120                 125

<210> SEQ ID NO 89
<211> LENGTH: 126
<212> TYPE: PRT
<213> ORGANISM: Artificial Sequence
<220> FEATURE:
<223> OTHER INFORMATION: Ab9 Heavy chain

<400> SEQUENCE: 89

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Asn Phe Thr Asn Tyr
            20                  25                  30

Trp Ile Gly Trp Val Arg Gln Leu Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ile Arg Val Ile Gly Phe Tyr Asp Ser Ser Pro Pro Leu
            100                 105                 110

Phe Asp Tyr Trp Gly Gln Gly Thr Leu Val Thr Val Ser Ser
        115                 120                 125

<210> SEQ ID NO 90
<211> LENGTH: 121
<212> TYPE: PRT
<213> ORGANISM: Artificial Sequence
<220> FEATURE:
<223> OTHER INFORMATION: Ab10 Heavy chain

<400> SEQUENCE: 90

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Gly Tyr
            20                  25                  30

Gly Ile His Trp Val Arg Gln Ala Pro Gly Lys Gly Leu Glu Trp Val
        35                  40                  45

Ala Leu Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

-continued

Leu Gln Met Asn Ser Leu Arg Ala Glu Asp Thr Ala Val Tyr Tyr Cys
                85                  90                  95

Ala Lys Asp Arg Asp Tyr Phe Gly Ser Gly Phe Phe Asp Tyr Trp Gly
            100                 105                 110

Gln Gly Thr Leu Val Thr Val Ser Ser
        115                 120

<210> SEQ ID NO 91
<211> LENGTH: 22
<212> TYPE: PRT
<213> ORGANISM: Artificial Sequence
<220> FEATURE:
<223> OTHER INFORMATION: Ab6 LFR1

<400> SEQUENCE: 91

Glu Leu Ala Leu Thr Gln Pro Pro Ser Val Ser Val Ala Pro Gly Lys
1               5                   10                  15

Thr Ala Lys Ile Thr Cys
            20

<210> SEQ ID NO 92
<211> LENGTH: 22
<212> TYPE: PRT
<213> ORGANISM: Artificial Sequence
<220> FEATURE:
<223> OTHER INFORMATION: Ab7 LFR1

<400> SEQUENCE: 92

Glu Leu Val Leu Thr Gln Pro Pro Ser Val Ser Ala Ala Pro Gly Gln
1               5                   10                  15

Lys Val Thr Ile Ser Cys
            20

<210> SEQ ID NO 93
<211> LENGTH: 22
<212> TYPE: PRT
<213> ORGANISM: Artificial Sequence
<220> FEATURE:
<223> OTHER INFORMATION: Ab8 LFR1

<400> SEQUENCE: 93

Glu Leu Ala Leu Thr Gln Pro Pro Ser Val Ser Val Ala Pro Ala Met
1               5                   10                  15

Thr Ala Lys Ile Thr Cys
            20

<210> SEQ ID NO 94
<211> LENGTH: 22
<212> TYPE: PRT
<213> ORGANISM: Artificial Sequence
<220> FEATURE:
<223> OTHER INFORMATION: Ab9 LFR1

<400> SEQUENCE: 94

Glu Leu Glu Leu Thr Gln Pro Pro Ser Val Ser Gly Thr Pro Gly Lys
1               5                   10                  15

Arg Val Ser Met Ser Cys
            20

<210> SEQ ID NO 95
<211> LENGTH: 25
<212> TYPE: PRT
<213> ORGANISM: Artificial Sequence

```
<220> FEATURE:
<223> OTHER INFORMATION: Ab10 LFR1

<400> SEQUENCE: 95

Glu Val Gln Leu Val Glu Ser Gly Gly Gly Val Val Gln Pro Gly Arg
1               5                   10                  15

Ser Leu Arg Leu Ser Cys Ala Ala Ser
            20                  25

<210> SEQ ID NO 96
<211> LENGTH: 25
<212> TYPE: PRT
<213> ORGANISM: Artificial Sequence
<220> FEATURE:
<223> OTHER INFORMATION: Ab6 HFR1

<400> SEQUENCE: 96

Gln Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 97
<211> LENGTH: 25
<212> TYPE: PRT
<213> ORGANISM: Artificial Sequence
<220> FEATURE:
<223> OTHER INFORMATION: Ab7 HFR1

<400> SEQUENCE: 97

Gln Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 98
<211> LENGTH: 25
<212> TYPE: PRT
<213> ORGANISM: Artificial Sequence
<220> FEATURE:
<223> OTHER INFORMATION: Ab8 HFR1

<400> SEQUENCE: 98

Gln Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 99
<211> LENGTH: 25
<212> TYPE: PRT
<213> ORGANISM: Artificial Sequence
<220> FEATURE:
<223> OTHER INFORMATION: Ab9 HFR1

<400> SEQUENCE: 99

Gln Val Gln Leu Val Gln Ser Gly Ala Glu Val Lys Lys Pro Gly Glu
1               5                   10                  15

Ser Leu Lys Ile Ser Cys Lys Gly Ser
            20                  25

<210> SEQ ID NO 100
<211> LENGTH: 25
<212> TYPE: PRT
```

<213> ORGANISM: Artificial Sequence
<220> FEATURE:
<223> OTHER INFORMATION: Ab10 HFR1

<400> SEQUENCE: 100

Glu Val Gln Leu Val Glu Ser Gly Gly Val Val Gln Pro Gly Arg
1               5                   10                  15

Ser Leu Arg Leu Ser Cys Ala Ala Ser
            20                  25

<210> SEQ ID NO 101
<211> LENGTH: 11
<212> TYPE: PRT
<213> ORGANISM: Artificial Sequence
<220> FEATURE:
<223> OTHER INFORMATION: Ab6 LCDR1

<400> SEQUENCE: 101

Gly Gly Asp Asp Ile Gly Ser Lys Thr Val Gln
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Ab7 LCDR1

<400> SEQUENCE: 102

Ser Gly Ser Ser Ser Asn Ile Gly Asn Asn Val Val Ser
1               5                   10

<210> SEQ ID NO 103
<211> LENGTH: 11
<212> TYPE: PRT
<213> ORGANISM: Artificial Sequence
<220> FEATURE:
<223> OTHER INFORMATION: Ab8 LCDR1

<400> SEQUENCE: 103

Gly Gly Asp Asp Ile Gly Ser Thr Thr Val Gln
1               5                   10

<210> SEQ ID NO 104
<211> LENGTH: 13
<212> TYPE: PRT
<213> ORGANISM: Artificial Sequence
<220> FEATURE:
<223> OTHER INFORMATION: Ab9 LCDR1

<400> SEQUENCE: 104

Ser Gly Ser Arg Ser Asn Ile Gly Gly Asn Val Val Asn
1               5                   10

<210> SEQ ID NO 105
<211> LENGTH: 11
<212> TYPE: PRT
<213> ORGANISM: Artificial Sequence
<220> FEATURE:
<223> OTHER INFORMATION: Ab10 LCDR1

<400> SEQUENCE: 105

Arg Ala Ser Gln Ser Ile Tyr Thr Tyr Leu Asn
1               5                   10

<210> SEQ ID NO 106

```
<211> LENGTH: 10
<212> TYPE: PRT
<213> ORGANISM: Artificial Sequence
<220> FEATURE:
<223> OTHER INFORMATION: Ab6 LCDR1

<400> SEQUENCE: 106

Gly Tyr Ile Phe Thr Asn Tyr Trp Ile Gly
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Ab7 LCDR1

<400> SEQUENCE: 107

Gly Tyr Ser Phe Thr Ser Tyr Trp Ile Gly
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Ab8 LCDR1

<400> SEQUENCE: 108

Gly Tyr Ile Phe Thr Asn Tyr Trp Ile Gly
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Ab9 LCDR1

<400> SEQUENCE: 109

Gly Tyr Asn Phe Thr Asn Tyr Trp Ile Gly
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Ab10 LCDR1

<400> SEQUENCE: 110

Gly Phe Thr Phe Ser Gly Tyr Gly Ile His
1               5                   10

<210> SEQ ID NO 111
<211> LENGTH: 15
<212> TYPE: PRT
<213> ORGANISM: Artificial Sequence
<220> FEATURE:
<223> OTHER INFORMATION: Ab6 LFR2

<400> SEQUENCE: 111

Trp Tyr Gln Gln Thr Ser Gly Gln Ala Pro Val Leu Val Val Tyr
1               5                   10                  15

<210> SEQ ID NO 112
<211> LENGTH: 15
```

```
<212> TYPE: PRT
<213> ORGANISM: Artificial Sequence
<220> FEATURE:
<223> OTHER INFORMATION: Ab7 LFR2

<400> SEQUENCE: 112

Trp Tyr Gln Gln Leu Pro Gly Thr Ala Pro Lys Leu Leu Ile Tyr
1               5                   10                  15

<210> SEQ ID NO 113
<211> LENGTH: 15
<212> TYPE: PRT
<213> ORGANISM: Artificial Sequence
<220> FEATURE:
<223> OTHER INFORMATION: Ab8 LFR2

<400> SEQUENCE: 113

Trp Tyr Gln Gln Thr Ser Gly Gln Ala Pro Val Leu Val Val Tyr
1               5                   10                  15

<210> SEQ ID NO 114
<211> LENGTH: 15
<212> TYPE: PRT
<213> ORGANISM: Artificial Sequence
<220> FEATURE:
<223> OTHER INFORMATION: Ab9 LFR2

<400> SEQUENCE: 114

Trp Tyr Gln Gln Leu Pro Gly Lys Ala Pro Lys Leu Phe Ile Tyr
1               5                   10                  15

<210> SEQ ID NO 115
<211> LENGTH: 15
<212> TYPE: PRT
<213> ORGANISM: Artificial Sequence
<220> FEATURE:
<223> OTHER INFORMATION: Ab10 LFR2

<400> SEQUENCE: 115

Trp Tyr His Gln Thr Pro Gly Lys Ala Pro Lys Leu Leu Ile Ser
1               5                   10                  15

<210> SEQ ID NO 116
<211> LENGTH: 13
<212> TYPE: PRT
<213> ORGANISM: Artificial Sequence
<220> FEATURE:
<223> OTHER INFORMATION: Ab6 HFR2

<400> SEQUENCE: 116

Trp Val Arg Gln Met Pro Gly Lys Gly Leu Glu Trp Met
1               5                   10

<210> SEQ ID NO 117
<211> LENGTH: 13
<212> TYPE: PRT
<213> ORGANISM: Artificial Sequence
<220> FEATURE:
<223> OTHER INFORMATION: Ab7 HFR2

<400> SEQUENCE: 117

Trp Val Arg Gln Met Pro Gly Lys Gly Leu Glu Trp Met
1               5                   10

<210> SEQ ID NO 118
<211> LENGTH: 13
<212> TYPE: PRT
```

```
<213> ORGANISM: Artificial Sequence
<220> FEATURE:
<223> OTHER INFORMATION: Ab8 HFR2

<400> SEQUENCE: 118

Trp Val Arg Gln Met Pro Gly Lys Gly Leu Glu Trp Met
1               5                   10

<210> SEQ ID NO 119
<211> LENGTH: 13
<212> TYPE: PRT
<213> ORGANISM: Artificial Sequence
<220> FEATURE:
<223> OTHER INFORMATION: Ab9 HFR2

<400> SEQUENCE: 119

Trp Val Arg Gln Leu Pro Gly Lys Gly Leu Glu Trp Met
1               5                   10

<210> SEQ ID NO 120
<211> LENGTH: 13
<212> TYPE: PRT
<213> ORGANISM: Artificial Sequence
<220> FEATURE:
<223> OTHER INFORMATION: Ab10 HFR2

<400> SEQUENCE: 120

Trp Val Arg Gln Ala Pro Gly Lys Gly Leu Glu Trp Val
1               5                   10

<210> SEQ ID NO 121
<211> LENGTH: 7
<212> TYPE: PRT
<213> ORGANISM: Artificial Sequence
<220> FEATURE:
<223> OTHER INFORMATION: Ab6 LCDR2

<400> SEQUENCE: 121

Asp Asp Ser Asp Arg Pro Ser
1               5

<210> SEQ ID NO 122
<211> LENGTH: 7
<212> TYPE: PRT
<213> ORGANISM: Artificial Sequence
<220> FEATURE:
<223> OTHER INFORMATION: Ab7 LCDR2

<400> SEQUENCE: 122

Asp Asp Asn Arg Arg Pro Ser
1               5

<210> SEQ ID NO 123
<211> LENGTH: 7
<212> TYPE: PRT
<213> ORGANISM: Artificial Sequence
<220> FEATURE:
<223> OTHER INFORMATION: Ab8 LCDR2

<400> SEQUENCE: 123

Asp Asp Ser Asp Arg Pro Ser
1               5

<210> SEQ ID NO 124
<211> LENGTH: 7
<212> TYPE: PRT
<213> ORGANISM: Artificial Sequence
```

```
<220> FEATURE:
<223> OTHER INFORMATION: Ab9 LCDR2

<400> SEQUENCE: 124

Asn Asn Asp Gln Arg Pro Ser
1               5

<210> SEQ ID NO 125
<211> LENGTH: 7
<212> TYPE: PRT
<213> ORGANISM: Artificial Sequence
<220> FEATURE:
<223> OTHER INFORMATION: Ab10 LCDR2

<400> SEQUENCE: 125

Ala Ala Ser Ser Leu Gln Ser
1               5

<210> SEQ ID NO 126
<211> LENGTH: 18
<212> TYPE: PRT
<213> ORGANISM: Artificial Sequence
<220> FEATURE:
<223> OTHER INFORMATION: Ab6 HCDR2

<400> SEQUENCE: 126

Gly Ile Ile Tyr Pro Gly Asp Ser Asp Thr Arg Tyr Ser Pro Ser Phe
1               5                   10                  15

Gln Gly

<210> SEQ ID NO 127
<211> LENGTH: 18
<212> TYPE: PRT
<213> ORGANISM: Artificial Sequence
<220> FEATURE:
<223> OTHER INFORMATION: Ab7 HCDR2

<400> SEQUENCE: 127

Gly Ile Ile Tyr Pro Gly Asp Ser Asp Thr Arg Tyr Ser Pro Ser Phe
1               5                   10                  15

Gln Gly

<210> SEQ ID NO 128
<211> LENGTH: 18
<212> TYPE: PRT
<213> ORGANISM: Artificial Sequence
<220> FEATURE:
<223> OTHER INFORMATION: Ab8 HCDR2

<400> SEQUENCE: 128

Gly Ile Ile Tyr Pro Gly Asp Ser Asp Thr Arg Tyr Ser Pro Ser Phe
1               5                   10                  15

Gln Gly

<210> SEQ ID NO 129
<211> LENGTH: 18
<212> TYPE: PRT
<213> ORGANISM: Artificial Sequence
<220> FEATURE:
<223> OTHER INFORMATION: Ab9 HCDR2

<400> SEQUENCE: 129

Gly Ile Ile Tyr Pro Gly Asp Ser Asp Thr Arg Tyr Ser Pro Ser Phe
1               5                   10                  15
```

Gln Gly

<210> SEQ ID NO 130
<211> LENGTH: 18
<212> TYPE: PRT
<213> ORGANISM: Artificial Sequence
<220> FEATURE:
<223> OTHER INFORMATION: Ab10 HCDR2

<400> SEQUENCE: 130

Ala Leu Ile Ser Tyr Asp Gly Ser Asn Lys Tyr Tyr Ala Asp Ser Val
1               5                   10                  15

Lys Gly

<210> SEQ ID NO 131
<211> LENGTH: 32
<212> TYPE: PRT
<213> ORGANISM: Artificial Sequence
<220> FEATURE:
<223> OTHER INFORMATION: Ab6 LFR3

<400> SEQUENCE: 131

Gly Ile Pro Glu Arg Phe Ser Gly Ala Asn Ser Gly Asn Thr Ala Thr
1               5                   10                  15

Leu Thr Ile Ser Arg Val Glu Ala Gly Asp Glu Ala Asp Tyr Tyr Cys
                20                  25                  30

<210> SEQ ID NO 132
<211> LENGTH: 32
<212> TYPE: PRT
<213> ORGANISM: Artificial Sequence
<220> FEATURE:
<223> OTHER INFORMATION: Ab7 LFR3

<400> SEQUENCE: 132

Gly Ile Pro Asp Arg Phe Ser Gly Ser Lys Ser Gly Thr Ser Ala Thr
1               5                   10                  15

Leu Asp Ile Thr Gly Leu Gln Thr Gly Asp Glu Ala Asp Tyr Tyr Cys
                20                  25                  30

<210> SEQ ID NO 133
<211> LENGTH: 32
<212> TYPE: PRT
<213> ORGANISM: Artificial Sequence
<220> FEATURE:
<223> OTHER INFORMATION: Ab8 LFR3

<400> SEQUENCE: 133

Gly Ile Pro Glu Arg Phe Ser Gly Ala Asn Ser Gly Asn Thr Ala Thr
1               5                   10                  15

Leu Thr Ile Ser Arg Val Glu Ala Gly Asp Glu Ala Asp Tyr Tyr Cys
                20                  25                  30

<210> SEQ ID NO 134
<211> LENGTH: 32
<212> TYPE: PRT
<213> ORGANISM: Artificial Sequence
<220> FEATURE:
<223> OTHER INFORMATION: Ab9 LFR3

<400> SEQUENCE: 134

Gly Val Pro Asp Arg Val Ser Gly Ser Lys Ser Gly Thr Ser Val Ser
1               5                   10                  15

Val Ala Ile Ser Gly Leu Gln Pro Glu Asp Glu Ala Asp Tyr Tyr Cys

<210> SEQ ID NO 135
<211> LENGTH: 32
<212> TYPE: PRT
<213> ORGANISM: Artificial Sequence
<220> FEATURE:
<223> OTHER INFORMATION: Ab10 LFR3

<400> SEQUENCE: 135

Gly Val Pro Ser Arg Phe Ser Gly Ser Gly Ser Gly Thr Asp Phe Thr
1               5                   10                  15
Leu Thr Ile Ser Ser Leu Gln Pro Glu Asp Phe Ala Thr Tyr Tyr Cys
            20                  25                  30

<210> SEQ ID NO 136
<211> LENGTH: 31
<212> TYPE: PRT
<213> ORGANISM: Artificial Sequence
<220> FEATURE:
<223> OTHER INFORMATION: Ab6 HFR3

<400> SEQUENCE: 136

Gln Val Thr Ile Ser Ala Asp Arg Ser Ile Ser Thr Ala Tyr Leu Gln
1               5                   10                  15
Trp Ser Ser Leu Lys Ala Ser Asp Thr Ala Met Tyr Tyr Cys Ala
            20                  25                  30

<210> SEQ ID NO 137
<211> LENGTH: 31
<212> TYPE: PRT
<213> ORGANISM: Artificial Sequence
<220> FEATURE:
<223> OTHER INFORMATION: Ab7 HFR3

<400> SEQUENCE: 137

Gln Val Thr Ile Ser Ala Asp Lys Ser Ile Ser Thr Ala Tyr Leu Gln
1               5                   10                  15
Trp Ser Ser Leu Lys Ala Ser Asp Thr Ala Met Tyr Tyr Cys Ala
            20                  25                  30

<210> SEQ ID NO 138
<211> LENGTH: 31
<212> TYPE: PRT
<213> ORGANISM: Artificial Sequence
<220> FEATURE:
<223> OTHER INFORMATION: Ab8 HFR3

<400> SEQUENCE: 138

Gln Val Thr Ile Ser Ala Asp Arg Ser Ile Ser Thr Ala Asn Leu Gln
1               5                   10                  15
Trp Ser Ser Leu Lys Ala Ser Asp Thr Ala Leu Tyr Tyr Cys Ala
            20                  25                  30

<210> SEQ ID NO 139
<211> LENGTH: 31
<212> TYPE: PRT
<213> ORGANISM: Artificial Sequence
<220> FEATURE:
<223> OTHER INFORMATION: Ab9 HFR3

<400> SEQUENCE: 139

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala
            20                  25                  30

<210> SEQ ID NO 140
<211> LENGTH: 31
<212> TYPE: PRT
<213> ORGANISM: Artificial Sequence
<220> FEATURE:
<223> OTHER INFORMATION: Ab10 HFR3

<400> SEQUENCE: 140

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala
            20                  25                  30

<210> SEQ ID NO 141
<211> LENGTH: 11
<212> TYPE: PRT
<213> ORGANISM: Artificial Sequence
<220> FEATURE:
<223> OTHER INFORMATION: Ab6 LCDR3

<400> SEQUENCE: 141

Gln Val Trp Asp Gly Arg Ser Asp His Val Val
1               5                   10

<210> SEQ ID NO 142
<211> LENGTH: 13
<212> TYPE: PRT
<213> ORGANISM: Artificial Sequence
<220> FEATURE:
<223> OTHER INFORMATION: Ab7 LCDR3

<400> SEQUENCE: 142

Ala Thr Trp Asp Gly Ser Leu Thr Ala Gly Arg Val Leu
1               5                   10

<210> SEQ ID NO 143
<211> LENGTH: 11
<212> TYPE: PRT
<213> ORGANISM: Artificial Sequence
<220> FEATURE:
<223> OTHER INFORMATION: Ab8 LCDR3

<400> SEQUENCE: 143

Gln Val Trp Asp Gly Arg Ser Asp His Val Val
1               5                   10

<210> SEQ ID NO 144
<211> LENGTH: 11
<212> TYPE: PRT
<213> ORGANISM: Artificial Sequence
<220> FEATURE:
<223> OTHER INFORMATION: Ab9 LCDR3

<400> SEQUENCE: 144

Ala Ala Trp Asp Asp Ile Leu Asn Gly Val Val
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Ab10 LCDR3

<400> SEQUENCE: 145

Gln Gln Tyr Ala Asp Val Pro Val Thr
1               5

<210> SEQ ID NO 146
<211> LENGTH: 22
<212> TYPE: PRT
<213> ORGANISM: Artificial Sequence
<220> FEATURE:
<223> OTHER INFORMATION: Ab6 HCDR3

<400> SEQUENCE: 146

Arg Leu Lys Leu Arg Gly Phe Ser Gly Gly Tyr Gly Ser Gly Arg Arg
1               5                   10                  15

Tyr Phe Asp Tyr Trp Gly
            20

<210> SEQ ID NO 147
<211> LENGTH: 22
<212> TYPE: PRT
<213> ORGANISM: Artificial Sequence
<220> FEATURE:
<223> OTHER INFORMATION: Ab7 HCDR3

<400> SEQUENCE: 147

Arg Leu Lys Leu Arg Gly Phe Ser Gly Gly Tyr Gly Ser Gly Ser Arg
1               5                   10                  15

Tyr Phe Asp Tyr Trp Gly
            20

<210> SEQ ID NO 148
<211> LENGTH: 22
<212> TYPE: PRT
<213> ORGANISM: Artificial Sequence
<220> FEATURE:
<223> OTHER INFORMATION: Ab8 HCDR3

<400> SEQUENCE: 148

Arg Leu Lys Leu Arg Gly Phe Ser Gly Gly Tyr Gly Ser Gly Arg Arg
1               5                   10                  15

Tyr Phe Asp Tyr Trp Gly
            20

<210> SEQ ID NO 149
<211> LENGTH: 20
<212> TYPE: PRT
<213> ORGANISM: Artificial Sequence
<220> FEATURE:
<223> OTHER INFORMATION: Ab9 HCDR3

<400> SEQUENCE: 149

Arg Ile Arg Val Ile Gly Phe Tyr Asp Ser Ser Pro Pro Pro Leu Phe
1               5                   10                  15

Asp Tyr Trp Gly
            20

<210> SEQ ID NO 150
<211> LENGTH: 15
<212> TYPE: PRT
<213> ORGANISM: Artificial Sequence
<220> FEATURE:
<223> OTHER INFORMATION: Ab10 HCDR3

<400> SEQUENCE: 150

```
Lys Asp Arg Asp Tyr Phe Gly Ser Gly Phe Phe Asp Tyr Trp Gly
1               5                   10                  15
```

<210> SEQ ID NO 151
<211> LENGTH: 10
<212> TYPE: PRT
<213> ORGANISM: Artificial Sequence
<220> FEATURE:
<223> OTHER INFORMATION: Ab6 LFR4

<400> SEQUENCE: 151

```
Phe Gly Gly Gly Thr Lys Leu Thr Val Leu
1               5                   10
```

<210> SEQ ID NO 152
<211> LENGTH: 10
<212> TYPE: PRT
<213> ORGANISM: Artificial Sequence
<220> FEATURE:
<223> OTHER INFORMATION: Ab7 LFR4

<400> SEQUENCE: 152

```
Phe Gly Ser Gly Thr Lys Leu Thr Val Leu
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: Ab8 LFR4

<400> SEQUENCE: 153

```
Phe Gly Gly Gly Thr Lys Leu Thr Val Leu
1               5                   10
```

<210> SEQ ID NO 154
<211> LENGTH: 10
<212> TYPE: PRT
<213> ORGANISM: Artificial Sequence
<220> FEATURE:
<223> OTHER INFORMATION: Ab9 LFR4

<400> SEQUENCE: 154

```
Phe Gly Gly Gly Thr Gln Leu Thr Val Leu
1               5                   10
```

<210> SEQ ID NO 155
<211> LENGTH: 10
<212> TYPE: PRT
<213> ORGANISM: Artificial Sequence
<220> FEATURE:
<223> OTHER INFORMATION: Ab10 LFR4

<400> SEQUENCE: 155

```
Phe Gly Gly Gly Thr Lys Leu Glu Ile Lys
1               5                   10
```

<210> SEQ ID NO 156
<211> LENGTH: 9
<212> TYPE: PRT
<213> ORGANISM: Artificial Sequence
<220> FEATURE:
<223> OTHER INFORMATION: Ab6 HFR4

<400> SEQUENCE: 156

```
Gln Gly Thr Leu Val Thr Val Ser Ser
```

<210> SEQ ID NO 157
<211> LENGTH: 9
<212> TYPE: PRT
<213> ORGANISM: Artificial Sequence
<220> FEATURE:
<223> OTHER INFORMATION: Ab7 HFR4

<400> SEQUENCE: 157

Gln Gly Thr Leu Val Thr Val Ser Ser
1               5

<210> SEQ ID NO 158
<211> LENGTH: 9
<212> TYPE: PRT
<213> ORGANISM: Artificial Sequence
<220> FEATURE:
<223> OTHER INFORMATION: Ab8 HFR4

<400> SEQUENCE: 158

Gln Gly Thr Leu Val Thr Val Ser Ser
1               5

<210> SEQ ID NO 159
<211> LENGTH: 9
<212> TYPE: PRT
<213> ORGANISM: Artificial Sequence
<220> FEATURE:
<223> OTHER INFORMATION: Ab9 HFR4

<400> SEQUENCE: 159

Gln Gly Thr Leu Val Thr Val Ser Ser
1               5

<210> SEQ ID NO 160
<211> LENGTH: 9
<212> TYPE: PRT
<213> ORGANISM: Artificial Sequence
<220> FEATURE:
<223> OTHER INFORMATION: Ab10 HFR4

<400> SEQUENCE: 160

Gln Gly Thr Leu Val Thr Val Ser Ser
1               5

<210> SEQ ID NO 161
<211> LENGTH: 744
<212> TYPE: DNA
<213> ORGANISM: Artificial Sequence
<220> FEATURE:
<223> OTHER INFORMATION: Ab1 scFv

<400> SEQUENCE: 161
gagctcacac tcacgcagtc tccagccacc ctgtctttgt ctccagggga aacagccacc      60
ctctcctgcg gggccagtca gagtgttagc accaactact tagcctggta ccagcagaaa     120
cctggcctgg cgcccaggct cctcatctat gatgcatcca gcagggccac tggcatccca     180
gacaggttca gtggcagtgg gtctgggaca gacttcactc tcaccatcag cagactggcg     240
cctgaagatt ctgcggtgta ttactgtcag caatatggta gctcacctct cactttcggc     300
ggagggacca agctggagat caaaggtggt tcctctagat cttcctcctc tggtggcggt     360
ggctcgggcg gtggtgggca ggtgcagctg gtgcagtctg ggcctgaggt gaagaagcct     420
gggtcctcgg tgaaggtctc ctgcaaggct tctggaggca ccttcagcac ctatgctatc     480
agctgggtgc gacaggcccc tggacaaggg cttgagtgga tgggagggat catccctatc    540
tctggtacag caaactacgc acagaaattc cagggcagag tcaccattac cgcggacgaa    600
tccacgagca cagcctacat ggagctgagc agcctgagat ctgaggacac ggccgtgtat    660
tactgtgcgg taccagtagt accagctgcc agcggcccctt ttgactactg gggccaggga    720
accctggtca ccgtctcctc agcc    744

<210> SEQ ID NO 162
<211> LENGTH: 777
<212> TYPE: DNA
<213> ORGANISM: Artificial Sequence
<220> FEATURE:
<223> OTHER INFORMATION: Ab2 scFv

<400> SEQUENCE: 162
gagctcgtgg tgacgcagcc gccctcagtg tctggggccc cagggcagag ggtcaccatc     60
tcctgttctg gaagcagctc caacatcgga aataatactg taaactggta ccagcagctc    120
ccaggaacgg cccccaaact cctcatctat agtaataatc agcggccctc agggtccct    180 gaccgattct ctggctccaa gtctggcacc tcagcctccc tggccatcac tgggctccag    240
gctgacgatg aggctgatta ttactgccag tcctttgaca gcagcctgaa tgattgggtg    300
ttcggcgggg gcaccaagct gaccgtccta ggcggtggtt cctctagatc ttcctcctct    360
ggtggcggtg gctcgggcgg tggtggggag gtgcagctgg tggagtctgg gggaggcctg    420
gtcaagcctg gggggtccct gagactctcc tgtgcagcct ctggattcac cttcagtagc    480
tatagcatga actgggtccg ccaggctcca gggaaggggc tggagtgggt ctcatccatt    540
agtagtagta gtcgttacat attctacgca gactcagtga agggccgatt caccatctcc    600
agagacaacg ccaagaactc actgtatctg caaatgaaca gcctgagagc cgaggacacg    660
gctgtgtatt actgtgcgag cctaggatat tgtagtggtg gtagctgcta cgggttcccg    720
gaaggtggga atgcttttga tatctgggc caagggacaa tggtcaccgt ctcttca    777

<210> SEQ ID NO 163
<211> LENGTH: 753
<212> TYPE: DNA
<213> ORGANISM: Artificial Sequence
<220> FEATURE:
<223> OTHER INFORMATION: Ab3 scFv

<400> SEQUENCE: 163
gagctcgagc tgactcagcc accctcagtg tctggggccc cagggcagag ggtcaccatc     60
tcctgcactg ggagcagctc caacatcggg gcaggttatg atgtacactg gtaccagcag    120
cttccaggaa cagcccccaa actcctcatc tatggtaaca gcaatcggcc ctcagggtc    180 cctgaccgat tctctggctc caagtctgac acctcagcct ccctggccat cagtgggctc    240
cggtccgagg atgaggctga ttattactgt gcagcatggg atgacagcct gaatggccag    300
gtggtattcg gcggaggcac caagctgacc gtcctaggcg tggttcctc tagatcttcc    360 tcctctggtg gcggtggctc gggcggtggt gggcaggtgc agctgcagga gtcgggccca    420
ggactggtga agccttcgga gaccctgtcc ctcacctgca ctgtctctgg tggtccttc    480 agtggttact actggagctg gatccgccag ccccaggaa aggggctgga gtggattggg    540
gaaatcattc atagtggaag caccaactac aacccgtccc tcaagagtcg agtcaccata    600
tcagtagaca cgtccaagaa ccaattctcc ctgaagctga gctctgtgac cgccgcggac    660

```
acggctgtgt attactgtgc gagaggtgat tattatgata gtagtggtgc ctttgactac    720
tggggccagg gaaccctggt caccgtctcc tca                                 753

<210> SEQ ID NO 164
<211> LENGTH: 774
<212> TYPE: DNA
<213> ORGANISM: Artificial Sequence
<220> FEATURE:
<223> OTHER INFORMATION: Ab4 scFv

<400> SEQUENCE: 164
gagctcgtgc tgactcagcc accttcagcg tctgggaccc ccgggcagag ggtcaccatc     60
tcttgttctg gaagcagctc caacatcgga agtaatactg taaactggta ccagcagctc    120
cccggaacgg cccccaaact cctcatctat agtaataatc agcggccccc agggggtccct   180 gaccgattct ctggctccaa gtctggcacc tcagcctccc tggccatcag tgggctccag    240
tctgaggatg aggctgatta ttactgccag tcctatgaca gcagcctgag ttatgtcttc    300
ggaactggca ccaaggtgac cgtcctaggc ggtggttcct ctagatcttc ctcctctggt    360
ggcggtggct cgggcggtgg tgggaggtg cagctggtgg agtctggggg aggcttggta     420
cagccggggg ggtccctgag actctcctgt gcagcctctg gattcacctt cagtagctat    480
agcatgaact gggtccgcca ggctccaggg aaggggctgg agtgggtctc atccattagt    540
agtagtagtc gttacatatt ctacgcagac tcagtgaagg gccgattcac catctccaga    600
gacaacgcca agaactcact gtatctgcaa atgaacagcc tgagagccga ggacacggct    660
gtgtattact gtgcgagcct aggatattgt agtggtggta gctgctacgg gttcccggaa    720
ggtgggaatg cttttgatat ctggggccaa gggacaatgg tcaccgtctc ttca          774

<210> SEQ ID NO 165
<211> LENGTH: 741
<212> TYPE: DNA
<213> ORGANISM: Artificial Sequence
<220> FEATURE:
<223> OTHER INFORMATION: Ab5 scFv

<400> SEQUENCE: 165
gagctcgtgg tgacccagga gccctcactg actgtgcccc caggagggac agtcactctc     60
acctgtggct ccagcactgg acctgtcacc actactcagt atcccatctg gttccagcag    120
aagcctggcc aggcccccag gacactcatt tatgatacca acaacagaca ccctggaca     180 cctgcccgct tctcaggctc cctccttggg ggcaaggctg ccctgaccct tcgggagcg     240 cagcctgagg atgacgctta gtattattgc ttgctcacct ctgctagcgc tccttgggtg    300
ttcggcggag gcaccaagct gaccgtccta ggcggtggtt cctctagatc ttcctcctct    360
ggtggcggtg gctcgggcgg tggtgggcag gtgcagctgg tgcagtctgg gggaggcttg    420
gtccagcctg gggggtccct gagactctcc tgttcagcct ctggattcac cttcagtagc    480
tatgctatgc actgggtccg ccaggctcca gggaagggac tggaatatgt ttcagctatt    540
agtagtgatg ggggtagcac atactacgca gactccgtga agggcagatt caccatctcc    600
agagacaatt ccaagaacac gctgtatctt caaatgagca gtctgagagc tgaggacacg    660
gctgtatatt actgtgtgaa cgatggcagc tcgaaccatt ttgactactg gggccaggga    720
accctggtca ccgtctcctc a                                              741

<210> SEQ ID NO 166
<211> LENGTH: 765
```

<212> TYPE: DNA
<213> ORGANISM: Artificial Sequence
<220> FEATURE:
<223> OTHER INFORMATION: Ab6 scFv

<400> SEQUENCE: 166

```
gagctcgccc tgactcagcc tccctccgtg tcagtggccc caggaaagac ggccaagatt      60
acctgtgggg gtgacgacat tggaagtaaa actgtgcaat ggtaccaaca gacctcaggc     120
caggcccctg tgctggtcgt ctatgacgat agcgaccggc cctcaggat ccctgagcga      180
ttctccggcg ccaactctgg aacacggcc accctgacca tcagcagggt cgaagccggg     240
gatgaggccg actattactg tcaggtgtgg acggcagaa gtgatcatgt ggttttcggc     300
ggagggacca gctgaccgt cctaggcggt ggttcctcta gatcttcctc ctctggtggc     360
ggtggctcgg cggtggtgg gcaggtgcag ctggtgcagt ctggagcaga ggtgaaaaag     420
cccggggagt ctctgaagat ctcctgtaag ggttctggat acatctttac caactactgg     480
atcggctggg tgcgccagat gcccgggaaa ggcctggagt ggatgggat catctatcct     540
ggtgactctg ataccagata cagcccgtcc ttccaaggcc aggtcaccat ctcagccgac     600
aggtccatca gcaccgccta cctgcagtgg agcagcctga aggcctcgga caccgccatg     660
tattactgtg cgagactaaa gctccggggg ttttcgggcg ctatggttc agggagacgc     720
tactttgact actggggcca gggaaccctg gtcaccgtct cctca                    765
```

<210> SEQ ID NO 167
<211> LENGTH: 777
<212> TYPE: DNA
<213> ORGANISM: Artificial Sequence
<220> FEATURE:
<223> OTHER INFORMATION: Ab7 scFv

<400> SEQUENCE: 167

```
gagctcgtgc tgacgcagcc gccctcagtg tctgcggccc caggactgaa ggtcaccatc      60
tcctgctctg gaagcagctc taacattggg aataatgttg tatcctggta ccagcaactc     120
ccaggaacag cccccaaact cctcatttat gacgataacc ggcgaccctc agggattcct     180
gaccgattct ctggctccaa gtctggcacg tcagccaccc tggacatcac cggactccag     240
actgggacg aggccgatta ctactgcgca acatgggatg cagcctgac tgctggccgt      300
gtgttgttcg gcagtggcac caagctgacc gtcctaggtg tggttcctc tagatcttcc     360
tcctctggtg gcggtggctc gggcggtggt gggcaggtgc agctggtgca gtctggagca     420
gaggtgaaaa agcccgggga gtctctgaag atctcctgta agggttctgg atacagcttt     480
accagctact ggatcggctg ggtgcgccag atgcccggga aaggcctgga gtggatgggg     540
atcatctatc ctggtgactc tgataccaga tacagcccgt ccttccaagg ccaggtcacc     600
atctcagccg acaagtccat cagcaccgcc tacctgcagt ggagcagcct gaaggcctcg     660
gacaccgcca tgtattactg tgcgagacta aagctccggg ggttttcggg cggctatggt     720
tcagggagcc gctactttga ctactggggc cagggaaccc tggtcaccgt ctcctca        777
```

<210> SEQ ID NO 168
<211> LENGTH: 765
<212> TYPE: DNA
<213> ORGANISM: Artificial Sequence
<220> FEATURE:
<223> OTHER INFORMATION: Ab8 scFv

<400> SEQUENCE: 168

```
gagctcgccc tgactcagcc tccctccgtg tcagtggccc agcaatgac ggccaagatt      60 acctgtgggg gtgacgacat tggaagtact actgtgcaat ggtaccaaca gacctcaggc    120
caggcccctg tgctggtcgt ctatgacgat agcgaccggc cctcagggat ccctgagcga    180
ttctccggcg ccaactctgg gaacacggcc accctgacca tcagcagggt cgaagccggg    240
gatgaggccg actattactg tcaggtgtgg gacggcagaa gtgatcatgt ggttttcggc    300
ggagggacca agctgaccgt cctaggcggt ggttcctcta gatcttcctc ctctggtggc    360
ggtggctcgg gcggtggtgg gcaggtgcag ctggtgcagt ctggagcaga ggtgaaaaag    420
cccggggagt ctctgaagat ctcctgtaag ggttctggat acatctttac caactactgg    480
atcggctggg tgcgccagat gcccgggaaa ggcctggagt ggatgggat catctatcct    540 ggtgactctg ataccagata cagcccgtcc ttccaaggcc aggtcaccat ctcagccgac    600
aggtccatca gcaccgccaa cctgcagtgg agcagcctga aggcctcgga caccgccctg    660
tattactgtg cgagactaaa gctccggggg ttttcgggcg ctatggttc agggagacgc    720 tactttgact actggggcca gggaaccctg gtcaccgtct cctca                    765
```

<210> SEQ ID NO 169
<211> LENGTH: 765
<212> TYPE: DNA
<213> ORGANISM: Artificial Sequence
<220> FEATURE:
<223> OTHER INFORMATION: Ab9 scFv

<400> SEQUENCE: 169

```
gagctcgagc tgactcagcc accctcagtg tctgggaccc ccgggaagag ggtcagtatg     60
tcttgttctg gaagtaggtc caacatcgga ggtaatgttg tgaactggta ccagcagctc    120
ccaggaaagg cccccaaact cttcatctac aataatgatc agcggccctc aggggtccct    180
gaccgagtct ctggctccaa gtcaggcacc tcagtctccg tggccatcag tgggctccag    240
cctgaagatg aggctgatta ttactgtgca gcttgggatg acatcctgaa tggtgtggtc    300
ttcggcggag ggacccagct gaccgtcctc ggcggtggtt cctctagatc ttcctcctct    360
ggtggcggtg gctcgggcgg tggtgggcag gtgcagctgg tgcagtctgg agcagaggtg    420
aaaaagcccg ggagtctct gaagatctcc tgtaagggtt ctggatacaa cttcaccaac    480
tactggatcg ggtgggtgcg ccagctgccc gggaaaggcc tggagtggat ggggatcatc    540
tatcctggtg actccgacac cagatatagc ccgtccttcc aaggccaggt caccatctca    600
gccgacaagt ccatcagcac cgcctacctg cagtggagca gcctgaaggc ctcggacacc    660
gccatgtatt actgtgcgag aattcgagtt atcggattct atgatagtag cccccccgccc    720 ttatttgact actggggcca gggaaccctg gtcaccgtct cctca                    765
```

<210> SEQ ID NO 170
<211> LENGTH: 738
<212> TYPE: DNA
<213> ORGANISM: Artificial Sequence
<220> FEATURE:
<223> OTHER INFORMATION: Ab10 scFv

<400> SEQUENCE: 170

```
gagctcgtga tgactcagtc tccatcttcc ctgtccgcat ctgtgggaga cacagtcacc     60
atcacttgcc gggcaagtca gagcatttac acctatttaa attggtatca ccagacacca    120
gggaaagccc ctaaactcct gatttctgct gcatctagtt tgcaaagtgg tgtcccatca    180
aggttcagtg gcagtgggtc tgggacagat ttcactctca ccatcagcag tctgcaacct    240
```

-continued

```
gaggattttg caacgtacta ctgtcaacag tatgcggatg tcccggtcac tttcggcgga    300
gggaccaagc tggagatcaa aggtggttcc tctagatctt cctcctctgg tggcggtggc    360
tcgggcggtg gtggggaggt gcagctggtg gagtctgggg gaggcgtggt ccagcctggg    420
aggtccctga gactctcctg tgcagcctct ggattcacct tcagtggcta tggcatacac    480
tgggtccgcc aggctccagg caaggggctg gagtgggtgg cacttatatc atatgatgga    540
agtaataaat actatgcaga ctccgtgaag ggccgattca ccatctccag agacaattcc    600
aagaacacgc tgtatctgca aatgaacagc ctgagagctg aggacacggc tgtgtattac    660
tgtgcgaaag atcgggatta ctttggttca gggttctttg actactgggg ccagggaacc    720
ctggtcaccg tctcctca                                                   738
```

<210> SEQ ID NO 171
<211> LENGTH: 1073
<212> TYPE: PRT
<213> ORGANISM: Artificial Sequence
<220> FEATURE:
<223> OTHER INFORMATION: membrane glycoprotein polyprotein of SFTSV

<400> SEQUENCE: 171

```
Met Met Lys Val Ile Trp Phe Ser Ser Leu Ile Cys Phe Val Ile Gln
  1               5                  10                  15

Cys Ser Gly Asp Ser Gly Pro Ile Ile Cys Ala Gly Pro Ile His Ser
             20                  25                  30

Asn Lys Ser Ala Asp Ile Pro His Leu Leu Gly Tyr Ser Glu Lys Ile
         35                  40                  45

Cys Gln Ile Asp Arg Leu Ile His Val Ser Ser Trp Leu Arg Asn His
     50                  55                  60

Ser Gln Phe Gln Gly Tyr Val Gly Gln Arg Gly Arg Ser Gln Val
 65                  70                  75                  80

Ser Tyr Tyr Pro Ala Glu Asn Ser Tyr Ser Arg Trp Ser Gly Leu Leu
                 85                  90                  95

Ser Pro Cys Asp Ala Asp Trp Leu Gly Met Leu Val Val Lys Lys Ala
            100                 105                 110

Lys Gly Ser Asp Met Ile Val Pro Gly Pro Ser Tyr Lys Gly Lys Val
        115                 120                 125

Phe Phe Glu Arg Pro Thr Phe Asp Gly Tyr Val Gly Trp Gly Cys Gly
    130                 135                 140

Ser Gly Lys Ser Arg Thr Glu Ser Gly Glu Leu Cys Ser Ser Asp Ser
145                 150                 155                 160

Gly Thr Ser Ser Gly Leu Leu Pro Ser Asp Arg Val Leu Trp Ile Gly
                165                 170                 175

Asp Val Ala Cys Gln Pro Met Thr Pro Ile Pro Glu Glu Thr Phe Leu
            180                 185                 190

Glu Leu Lys Ser Phe Ser Gln Ser Glu Phe Pro Asp Ile Cys Lys Ile
        195                 200                 205

Asp Gly Ile Val Phe Asn Gln Cys Glu Gly Glu Ser Leu Pro Gln Pro
    210                 215                 220

Phe Asp Val Ala Trp Met Asp Val Gly His Ser His Lys Ile Ile Met
225                 230                 235                 240

Arg Glu His Lys Thr Lys Trp Val Gln Glu Ser Ser Ser Lys Asp Phe
                245                 250                 255

Val Cys Tyr Lys Glu Gly Thr Gly Pro Cys Ser Glu Ser Glu Glu Lys
            260                 265                 270
```

-continued

```
Thr Cys Lys Thr Ser Gly Ser Cys Arg Gly Asp Met Gln Phe Cys Lys
        275                 280                 285
Val Ala Gly Cys Glu His Gly Glu Glu Ala Ser Glu Ala Lys Cys Arg
    290                 295                 300
Cys Ser Leu Val His Lys Pro Gly Glu Val Val Ser Tyr Gly Gly
305                 310                 315                 320
Met Arg Val Arg Pro Lys Cys Tyr Gly Phe Ser Arg Met Met Ala Thr
                325                 330                 335
Leu Glu Val Asn Gln Pro Glu Gln Arg Ile Gly Gln Cys Thr Gly Cys
                340                 345                 350
His Leu Glu Cys Ile Asn Gly Gly Val Arg Leu Ile Thr Leu Thr Ser
            355                 360                 365
Glu Leu Lys Ser Ala Thr Val Cys Ala Ser His Phe Cys Ser Ser Ala
        370                 375                 380
Thr Ser Gly Lys Lys Ser Thr Glu Ile Gln Phe His Ser Gly Ser Leu
385                 390                 395                 400
Val Gly Lys Thr Ala Ile His Val Lys Gly Ala Leu Val Asp Gly Thr
                405                 410                 415
Glu Phe Thr Phe Glu Gly Ser Cys Met Phe Pro Asp Gly Cys Asp Ala
            420                 425                 430
Val Asp Cys Thr Phe Cys Arg Glu Phe Leu Lys Asn Pro Gln Cys Tyr
        435                 440                 445
Pro Ala Lys Lys Trp Leu Phe Ile Ile Val Ile Leu Leu Gly Tyr
    450                 455                 460
Ala Gly Leu Met Leu Leu Thr Asn Val Leu Lys Ala Ile Gly Ile Trp
465                 470                 475                 480
Gly Ser Trp Val Ile Ala Pro Val Lys Leu Ile Phe Ala Ile Ile Lys
                485                 490                 495
Lys Leu Met Arg Ala Val Ser Cys Leu Met Gly Lys Leu Met Asp Arg
                500                 505                 510
Gly Arg Gln Val Ile His Glu Glu Ile Gly Glu Asn Arg Glu Gly Asn
            515                 520                 525
Gln Asp Asp Val Arg Ile Glu Met Ala Arg Pro Arg Val Arg His
    530                 535                 540
Trp Met Tyr Ser Pro Val Ile Leu Thr Ile Leu Ala Ile Gly Leu Ala
545                 550                 555                 560
Glu Ser Cys Asp Glu Met Val His Ala Asp Ser Lys Leu Val Ser Cys
                565                 570                 575
Arg Gln Gly Ser Gly Asn Met Lys Glu Cys Val Thr Thr Gly Arg Ala
            580                 585                 590
Leu Leu Pro Ala Val Asn Pro Gly Gln Glu Ala Cys Leu His Phe Thr
        595                 600                 605
Ala Pro Gly Ser Pro Asp Ser Lys Cys Leu Lys Ile Lys Val Lys Arg
    610                 615                 620
Ile Asn Leu Lys Cys Lys Lys Ser Ser Ser Tyr Phe Val Pro Asp Ala
625                 630                 635                 640
Arg Ser Arg Cys Thr Ser Val Arg Arg Cys Arg Trp Ala Gly Asp Cys
                645                 650                 655
Gln Ser Gly Cys Pro Pro His Phe Thr Ser Asn Ser Phe Ser Asp Asp
            660                 665                 670
Trp Ala Gly Lys Met Asp Arg Ala Gly Leu Gly Phe Ser Gly Cys Ser
        675                 680                 685
```

```
Asp Gly Cys Gly Gly Ala Ala Cys Gly Cys Phe Asn Ala Ala Pro Ser
690                 695                 700

Cys Ile Phe Trp Arg Lys Trp Val Glu Asn Pro His Gly Ile Ile Trp
705                 710                 715                 720

Lys Val Ser Pro Cys Ala Ala Trp Val Pro Ser Ala Val Ile Glu Leu
            725                 730                 735

Thr Met Pro Ser Gly Glu Val Arg Thr Phe His Pro Met Ser Gly Ile
            740                 745                 750

Pro Thr Gln Val Phe Lys Gly Val Ser Val Thr Tyr Leu Gly Ser Asp
            755                 760                 765

Met Glu Val Ser Gly Leu Thr Asp Leu Cys Glu Ile Glu Glu Leu Lys
770                 775                 780

Ser Lys Lys Leu Ala Leu Ala Pro Cys Asn Gln Ala Gly Met Gly Val
785                 790                 795                 800

Val Gly Lys Val Gly Glu Ile Gln Cys Ser Ser Glu Glu Ser Ala Arg
                805                 810                 815

Thr Ile Lys Lys Asp Gly Cys Ile Trp Asn Ala Asp Leu Val Gly Ile
            820                 825                 830

Glu Leu Arg Val Asp Asp Ala Val Cys Tyr Ser Lys Ile Thr Ser Val
            835                 840                 845

Glu Ala Val Ala Asn Tyr Ser Ala Ile Pro Thr Thr Ile Gly Gly Leu
850                 855                 860

Arg Phe Glu Arg Ser His Asp Ser Gln Gly Lys Ile Ser Gly Ser Pro
865                 870                 875                 880

Leu Asp Ile Thr Ala Ile Arg Gly Ser Phe Ser Val Asn Tyr Arg Gly
            885                 890                 895

Leu Arg Leu Ser Leu Ser Glu Ile Thr Ala Thr Cys Thr Gly Glu Val
                900                 905                 910

Thr Asn Val Ser Gly Cys Tyr Ser Cys Met Thr Gly Ala Lys Val Ser
            915                 920                 925

Ile Lys Leu His Ser Ser Lys Asn Ser Thr Ala His Val Arg Cys Lys
930                 935                 940

Gly Asp Glu Thr Ala Phe Ser Val Leu Glu Gly Val His Ser Tyr Thr
945                 950                 955                 960

Val Ser Leu Ser Phe Asp His Ala Val Val Asp Glu Gln Cys Gln Leu
            965                 970                 975

Asn Cys Gly Gly His Glu Ser Gln Val Thr Leu Lys Gly Asn Leu Ile
            980                 985                 990

Phe Leu Asp Val Pro Lys Phe Val Asp Gly Ser Tyr Met Gln Thr Tyr
995                 1000                1005

His Ser Thr Val Pro Thr Gly Ala Asn Ile Pro Ser Pro Thr Asp
    1010                1015                1020

Trp Leu Asn Ala Leu Phe Gly Asn Gly Leu Ser Arg Trp Ile Leu
    1025                1030                1035

Gly Val Ile Gly Val Leu Leu Gly Gly Leu Ala Leu Phe Phe Met
    1040                1045                1050

Ile Met Ser Leu Phe Lys Leu Gly Thr Lys Gln Val Phe Arg Ser
    1055                1060                1065

Arg Thr Lys Leu Ala
    1070
```

ANTIBODY THAT BINDS TO ENVELOPE GLYCOPROTEIN OF SEVERE FEVER WITH THROMBOCYTOPENIA SYNDROME VIRUS AND USE FOR SAME

CROSS-REFERENCE TO RELATED APPLICATIONS

This application is a national phase application of PCT Application No. PCT/KR2017/003156, filed on Mar. 23, 2017, which claims the benefit and priority to Korean patent application No. 10-2016-0034727, filed on Mar. 23, 2016. The entire disclosures of the applications identified in this paragraph are incorporated herein by references.

TECHNICAL FIELD

The present invention relates to an antibody which specifically binds to the envelope glycoprotein of severe fever with thrombocytopenia syndrome virus (SFTSV), the pathogen of severe fever with thrombocytopenia syndrome (SFTS), and is used in order to detect or diagnosis SFTSV and treat SFTS.

BACKGROUND

Severe Fever with Thrombocytopenia Syndrome (SFTS) is a new kind of mite-mediated infectious disease, and is mostly occurred by Severe Fever with Thrombocytopenia Syndrome Virus (SFTSV) mediated by *Haemaphysalis longicornis* or *Amblyomma testudinarium*. SFTS was firstly reported in China in 2009, and the disease and virus was reported in Japan and Korea in 2012. The main symptoms of SFTS are fever, abdominal pain, nausea, vomiting, thrombocytopenia or leukopenia, etc., and in case of serious case, multiple organ failure may occur and result in death. SFTS has consistently occurred in China, Japan or Korea every year, and the fatality rate caused thereby is very high, and it mostly occurs in the period between spring and summer. A black-stripped field mouse is probable as the wild host of SFTSV, and it was presumed that domestic animals can play a role of host, since the serum antibody was found at the high ratio in domestic animals such as goat, cow, dog or chicken, etc. in the major outbreak areas of China. It has been reported that the infection from person to person occurred by mediating a body fluid of an infected person, but there is no approved therapeutic agent or prevention method to effectively treat SFTS until now.

There is a method of confirming an anti-SFTSV antibody titer in blood to confirm SFTS infection. Then the anti-SFTSV antibody titer is mostly measured with an antibody for N protein of SFTSV. The antibody is an antibody for SFTSV internal protein exposed when SFTSV becomes extinct. Thus, the conventional diagnosis by confirming the anti-SFTSV antibody titer has limitation that the existence of virus which is alive and actively acts cannot be accurately figured out. As another method of diagnosing SFTS, the method for detecting the RNA sequence of SFTSV in a subject derived from a human body has been known as having high accuracy, but it has a difficulty to isolate virus RNA of good quality from the subject.

On the other hand, International patent publication No. 2015/053455 (WO2015/053455A1) discloses the method for detecting an antibody for SFTSV, but specifically it does not disclose to which antigen of SFTSV the antibody binds and the neutralization activity of the antibody at all.

Thus, the development of an antibody or method which can effectively detect, isolate or purify SFTSV by recovering limitations of an inaccurate virus titer measurement method of conventional enzyme immunoreaction diagnosis method detecting the amount of killed SFTSV protein, or conventional low purity of virus RNA isolation method in blood is need.

DISCLOSURE

Technical Problem

The problem to be solved by the present invention is to provide an antibody which can effectively detect or diagnose SFTSV and treat SFTS. In addition, the other problem to be solved by the present invention is to provide an antibody which specifically binds to SFTSV, particularly an envelope glycoprotein of SFTSV.

Technical Solution

To solve the technical problems, the present invention provides a novel antibody which specifically binds to SFTSV, particularly its envelope glycoprotein. In addition, the present invention provides a method for effectively detecting, isolating or purifying SFTSV using the antibody. In addition, the present invention, a method for effectively preventing or treating SFTS using the antibody.

As the result that the present inventors have made extensive efforts to overcome the limitations of conventional diagnosis methods of SFTSV, they found a novel antibody which specifically binds to an envelope glycoprotein of SFTSV, particularly Gc or Gn, and found that SFTSV can be effectively detected using it, to complete the present invention.

SFTSV is a minus single strand RNA virus, and belongs to Bunyaviridae family, *phlebovirus* species. The virus is a globular virus of 80-100 nm diameter and uses *Haemaphysalis longicornis* as a mediator. The genome of the virus consists of large (L), Medium (M) and small (S) segments, and these encode 6 proteins of RNA dependent RNA polymerase (RdRp), glycoprotein precursor (M), glycoprotein N (Gn), glycoprotein C (Gc), nucleocapsid protein (NP) and non-structural protein (NSs).

In the present invention, an "antibody" may include whole antibodies and any antigen binding portion or single chains thereof. A naturally occurring "antibody" is a glycoprotein comprising at least two heavy chains (H) and two light chains (L) interconnected by disulfide bonds. Each heavy chain consists of a heavy chain variable region (VH) and a heavy chain constant region (CH). The heavy chain constant region consists of three domains, CH1, CH2 and CH3. Each light chain consists of a light chain variable region (VL) and a light chain constant region (CL). The light chain constant region consists of one domain, CL. The VH and VL regions may be further subdivided into regions of hypervariability, referred to as complementarity determining regions (CDR), interspersed with regions that are more conserved, referred to as framework regions (FR). Each VH and VL consists of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen.

The present invention provides an antibody which specifically binds to an envelope glycoprotein of SFTSV, particularly an envelope glycoprotein of SFTSV, Gc or Gn. Preferably, the antibody may be comprise a specific amino acid sequence as follows or consists of them. In addition, certain modifications which are obvious in constant regions of heavy chains and light chains are included in the scope of the present invention in the range having same or similar binding specificity. Furthermore, as each of those antibodies can bind to the envelope glycoprotein of SFTSV, an antibody binding to other envelope glycoproteins of SFTSV of the present invention can be produced by mixing and matching VH, VL, full length light chain and full length heavy chain sequences (amino acid sequences and nucleotide sequences encoding the amino acid sequences).

In one example, the amino acid sequences of antibody clones (Ab1-5) which binds to Gc envelope glycoprotein of the present invention are shown in the following Tables 1-8.

Amino acid sequences of light chains and heavy chains binding to Gc envelope glycoprotein.

Amino acid sequences of light chain or heavy chain framework region 1 (LFR1 or HFR1) of the antibody binding to Gc envelope glycoprotein.

TABLE 2

| SEQ ID NO | Antibody and site | Sequence |
| --- | --- | --- |
| 11 | LFR1 of Ab1 | ELTLTQSPATLSLSPGETATLSC |
| 12 | LFR1 of Ab2 | ELVVTQPPSVSGAPGQRVTISC |
| 13 | LFR1 of Ab3 | ELELTQPPSVSGAPGQRVTISC |
| 14 | LFR1 of Ab4 | ELVLTQPPSASGTPGQRVTISC |
| 15 | LFR1 of Ab5 | ELVVTQEPSLTVPPGGTVTLTC |
| 16 | HFR1 of Ab1 | QVQLVQSGPEVKKPGSSVKVSCKAS |
| 17 | HFR1 of Ab2 | EVQLVESGGGLVKPGGSLRLSCAAS |

TABLE 1

| SEQ ID NO | Antibody and site | Sequence |
| --- | --- | --- |
| 1 | light chain of Ab1 | ELTLTQSPATLSLSPGETATLSC GASQSVSTNYLA WYQQKPGLAPRLLIY DASSRAT GIPDRFSGSGSGTDFTLTISRLAPEDSAVYYC QQYGSSPLT FGGGTKLEIK |
| 2 | light chain of Ab2 | ELVVTQPPSVSGAPGQRVTISC SGSSSNIGNNTVN WYQQLPGTAPKLLIY SNNQRPS GVPDRFSGSKSGTSASLAITGLQADDEADYYC QSFDSSLNDWV FGGGTKLTVL |
| 3 | light chain of Ab3 | ELELTQPPSVSGAPGQRVTISC TGSSSNIGAGYDVH WYQQLPGTAPKLLIY GNSNRPS GVPDRFSGSKSDTSASLAISGLRSEDEADYYC AAWDDSLNGQVV FGGGTKLTVL |
| 4 | light chain of Ab4 | ELVLTQPPSASGTPGQRVTISC SGSSSNIGSNTVN WYQQLPGTAPKLLIY SNNQRPP GVPDRFSGSKSGTSASLAISGLQSEDEADYYC QSYDSSLSYV FGTGTKVTVL |
| 5 | light chain of Ab5 | ELVVTQEPSLTVPPGGTVTLTC GSSTGPVTTTQYPY WFQQKPGQAPRTLIY DTNNRHP WTPARFSGSLLGGKAALTLSGAQPEDDA-YYC LLTSASAPWV FGGGTKLTVL |
| 6 | heavy chain of Ab1 | QVQLVQSGPEVKKPGSSVKVSCKAS GGTFSTYAIS WVRQAPGQGLEWMG GIIPISGTANYAQKFQG RVTITADESTSTAYMELSSLRSEDTAVYYCA VPV--------- VPAASGPFDYWG QGTLVTVSS |
| 7 | heavy chain of Ab2 | EVQLVESGGGLVKPGGSLRLSCAAS GFTFSSYSMN WVRQAPGKGLEWVS SISSSSRYIFYADSVKG RFTISRDNAKNSLYLQMNSLRAEDTAVYYCA SLGYCSGGSCYGFPEGGNAFDIWG QGTMVTVSS |
| 8 | heavy chain of Ab3 | QVQLQESGPGLVKPSETLSLTCTVS GGSFSGYYWS WIRQPPGKGLEWIG EIIHSGSTNYNPSLKS RVTISVDTSKNQFSLKLSSVTAADTAVYYCA RGDYYD--------- SSGAFDYWG QGTLVTVSS EVQLVESGGGLVQPGGSLRLSCAAS GFTFSSYSMN |
| 9 | heavy chain of Ab4 | WVRQAPGKGLEWVS SISSSSRYIFYADSVKG RFTISRDNAKNSLYLQMNSLRAEDTAVYY-- SLGYCSGGSCYGFPEGGNAFDIWG QGTMVTVSS |
| 10 | heavy chain of Ab5 | QVQLVQSGGGLVQPGGSLRLSCSAS GFTFSSYAMH WVRQAPGKGLEYVS AISSDGGSTYYADSVKG RFTISRDNSKNTLYLQMSSLRAEDTAVYYCV NDG----------- SSNHFDYWG QGTLVTVSS |

TABLE 2 -continued

| SEQ ID NO | Antibody and site | Sequence |
|---|---|---|
| 18 | HFR1 of Ab3 | QVQLQESGPGLVKPSETLSLTCTVS |
| 19 | HFR1 of Ab4 | EVQLVESGGGLVQPGGSLRLSCAAS |
| 20 | HFR1 of Ab5 | QVQLVQSGGGLVQPGGSLRLSCSAS |

Amino acid sequences of light chain or heavy chain complementarity determining region 1 (LCDR1 or HCDR1) of the antibody binding to Gc envelope glycoprotein.

TABLE 3

| SEQ ID NO | Antibody and site | Sequence |
|---|---|---|
| 21 | LCDR1 of Ab1 | GASQSVSTNYLA |
| 22 | LCDR1 of Ab2 | SGSSSNIGNNTVN |
| 23 | LCDR1 of Ab3 | TGSSSNIGAGYDVH |
| 24 | LCDR1 of Ab4 | SGSSSNIGSNTVN |
| 25 | LCDR1 of Ab5 | GSSTGPVTTTQYPY |
| 26 | HCDR1 of Ab1 | GGTFSTYAIS |
| 27 | HCDR1 of Ab2 | GFTFSSYSMN |
| 28 | HCDR1 of Ab3 | GGSFSGYYWS |
| 29 | HCDR1 of Ab4 | GFTFSSYSMN |
| 30 | HCDR1 of Ab5 | GFTFSSYAMH |

Amino acid sequences of light chain or heavy chain framework region 2 (LFR2 or HFR2) of the antibody binding to Gc envelope glycoprotein.

TABLE 4

| SEQ ID NO | Antibody and site | Sequence |
|---|---|---|
| 31 | LFR2 of Ab1 | WYQQKPGLAPRLLIY |
| 32 | LFR2 of Ab2 | WYQQLPGTAPKLLIY |
| 33 | LFR2 of Ab3 | WYQQLPGTAPKLLIY |
| 34 | LFR2 of Ab4 | WYQQLPGTAPKLLIY |
| 35 | LFR2 of Ab5 | WFQQKPGQAPRTLIY |
| 36 | HFR2 of Ab1 | WVRQAPGQGLEWMG |
| 37 | HFR2 of Ab2 | WVRQAPGKGLEWVS |
| 38 | HFR2 of Ab3 | WIRQPPGKGLEWIG |
| 39 | HFR2 of Ab4 | WVRQAPGKGLEWVS |
| 40 | HFR2 of Ab5 | WVRQAPGKGLEYVS |

Amino acid sequences of light chain or heavy chain complementarity determining region 2 (LCDR2 or HCDR2) of the antibody binding to Gc envelope glycoprotein.

TABLE 5

| SEQ ID NO | Antibody and site | Sequence |
|---|---|---|
| 41 | LCDR2 of Ab1 | DASSRAT |
| 42 | LCDR2 of Ab2 | SNNQRPS |
| 43 | LCDR2 of Ab3 | GNSNRPS |
| 44 | LCDR2 of Ab4 | SNNQRPP |
| 45 | LCDR2 of Ab5 | DTNNRHP |
| 46 | HCDR2 of Ab1 | GIIPISGTANYAQKFQG |
| 47 | HCDR2 of Ab2 | SISSSSRYIFYADSVKG |
| 48 | HCDR2 of Ab3 | EIIHSGSTNYNPSLKS |
| 49 | HCDR2 of Ab4 | SISSSSRYIFYADSVKG |
| 50 | HCDR2 of Ab5 | AISSDGGSTYYADSVKG |

Amino acid sequences of light chain or heavy chain framework region 3 (LFR3 or HFR3) of the antibody binding to Gc envelope glycoprotein.

TABLE 6

| SEQ ID NO | Antibody and site | Sequence |
|---|---|---|
| 51 | LFR3 of Ab1 | GIPDRFSGSGSGTDFTLTISRLAPEDSAVYYC |
| 52 | LFR3 of Ab2 | GVPDRFSGSKSGTSASLAITGLQADDEADYYC |
| 53 | LFR3 of Ab3 | GVPDRFSGSKSDTSASLAISGLRSEDEADYYC |
| 54 | LFR3 of Ab4 | GVPDRFSGSKSGTSASLAISGLQSEDEADYYC |
| 55 | LFR3 of Ab5 | WTPARFSGSLLGGKAALTLSGAQPEDDA-YYC |
| 56 | HFR3 of Ab1 | RVTITADESTSTAYMELSSLRSEDTAVYYCA |
| 57 | HFR3 of Ab2 | RFTISRDNAKNSLYLQMNSLRAEDTAVYYCA |
| 58 | HFR3 of Ab3 | RVTISVDTSKNQFSLKLSSVTAADTAVYYCA |
| 59 | HFR3 of Ab4 | RFTISRDNAKNSLYLQMNSLRAEDTAVYY-- |
| 60 | HFR3 of Ab5 | RFTISRDNSKNTLYLQMSSLRAEDTAVYYCV |

Amino acid sequences of light chain or heavy chain complementarity determining region 3 (LCDR3 or HCDR3) of the antibody binding to Gc envelope glycoprotein.

TABLE 7

| SEQ ID NO | Antibody and site | Sequence |
|---|---|---|
| 61 | LCDR3 of Ab1 | QQYGSSPLT |
| 62 | LCDR3 of Ab2 | QSFDSSLNDWV |
| 63 | LCDR3 of Ab3 | AAWDDSLNGQVV |
| 64 | LCDR3 of Ab4 | QSYDSSLSYV |
| 65 | LCDR3 of Ab5 | LLTSASAPWV |
| 66 | HCDR3 of Ab1 | VPV---------VPAASGPFDYWG |

TABLE 7-continued

| SEQ ID NO | Antibody and site | Sequence |
|---|---|---|
| 67 | HCDR3 of Ab2 | SLGYCSGGSCYGFPEGGNAFDIWG |
| 68 | HCDR3 of Ab3 | RGDYYD---------SSGAFDYWG |
| 69 | HCDR3 of Ab4 | SLGYCSGGSCYGFPEGGNAFDIWG |
| 70 | HCDR3 of Ab5 | NDG------------SSNHFDYWG |

Amino acid sequences of light chain or heavy chain framework region 4 (LFR4 or HFR4) of the antibody binding to Gc envelope glycoprotein.

TABLE 8

| SEQ ID NO | Antibody and site | Sequence |
|---|---|---|
| 71 | LFR4 of Ab1 | FGGGTKLEIK |
| 72 | LFR4 of Ab2 | FGGGTKLTVL |
| 73 | LFR4 of Ab3 | FGGGTKLTVL |
| 74 | LFR4 of Ab4 | FGTGTKVTVL |
| 75 | LFR4 of Ab5 | FGGGTKLTVL |
| 76 | HFR4 of Ab1 | QGTLVTVSS |
| 77 | HFR4 of Ab2 | QGTMVTVSS |
| 78 | HFR4 of Ab3 | QGTLVTVSS |
| 79 | HFR4 of Ab4 | QGTMVTVSS |
| 80 | HFR4 of Ab5 | QGTLVTVSS |

In some exemplary embodiments, the antibody specifically binding to the envelope glycoprotein of SFTSV, Gc may comprise a light chain comprising any one of amino acid sequences selected from the group consisting of SEQ ID NOs 1, 2, 3, 4 and 5, and a heavy chain comprising any one of amino acid sequences selected from the group consisting of SEQ ID NOs 6, 7, 8, 9 and 10. The antibody consisting of these specific sequences can specifically and effectively bind to the envelope glycoprotein, Gc, and thus can be very usefully used for detection of SFTSV.

In another exemplary embodiment, preferably, the antibody which specifically binds to the envelope glycoprotein of SFTSV, Gc of the present invention can be provided as an antibody comprising a light chain comprising an amino acid sequence of SEQ ID NO 1 and a heavy chain comprising an amino acid of SEQ ID NO 6, an antibody comprising a light chain comprising an amino acid sequence of SEQ ID NO 2 and a heavy chain comprising an amino acid of SEQ ID NO 7, an antibody comprising a light chain comprising an amino acid sequence of SEQ ID NO 3 and a heavy chain comprising an amino acid of SEQ ID NO 8, an antibody comprising a light chain comprising an amino acid sequence of SEQ ID NO 4 and a heavy chain comprising an amino acid of SEQ ID NO 9, and an antibody comprising a light chain comprising an amino acid sequence of SEQ ID NO 5 and a heavy chain comprising an amino acid of SEQ ID NO 10.

In another exemplary embodiment, the antibody which specifically binds to the envelope glycoprotein of SFTSV, Gc of the present invention can comprise a light chain complementarity determining region 1 (LCDR1) comprising any one of amino acid sequences selected from the group consisting of SEQ ID NOs 21, 22, 23, 24 and 25, a light chain complementarity determining region 2 (LCDR2) comprising any one of amino acid sequences selected from the group consisting of SEQ ID NOs 41, 42, 43, 44 and 45, a light chain complementarity determining region 3 (LCDR3) comprising any one of amino acid sequences selected from the group consisting of SEQ ID NOs 61, 62, 63, 64 and 65, a heavy chain complementarity determining region 1 (HCDR1) comprising any one of amino acid sequences selected from the group consisting of SEQ ID NOs 26, 27, 28, 29 and 30, a heavy chain complementarity determining region 2 (HCDR2) comprising any one of amino acid sequences selected from the group consisting of SEQ ID NOs 46, 47, 48, 49 and 50, and a heavy chain complementarity determining region 3 (HCDR3) comprising any one of amino acid sequences selected from the group consisting of SEQ ID NOs 66, 67, 68, 69 and 70.

In another exemplary embodiment, the antibody which specifically binds to the envelope glycoprotein of SFTSV, Gc of the present invention can be provided as an antibody comprising a light chain complementarity determining region 1 (LCDR1) of SEQ ID NO 21, a light chain complementarity determining region 2 (LCDR2) of SEQ ID NO 41, a light chain complementarity determining region 3 (LCDR3) of SEQ ID NO 61, a heavy chain complementarity determining region 1 (HCDR1) of SEQ ID NO 26, a heavy chain complementarity determining region 2 (HCDR2) of SEQ ID NO 46, and a heavy chain complementarity determining region 3 (HCDR3) of SEQ ID NO 66; an antibody comprising a light chain complementarity determining region 1 (LCDR1) of SEQ ID NO 22, a light chain complementarity determining region 2 (LCDR2) of SEQ ID NO 42, a light chain complementarity determining region 3 (LCDR3) of SEQ ID NO 62, a heavy chain complementarity determining region 1 (HCDR1) of SEQ ID NO 27, a heavy chain complementarity determining region 2 (HCDR2) of SEQ ID NO 47, and a heavy chain complementarity determining region 3 (HCDR3) of SEQ ID NO 67; an antibody comprising a light chain complementarity determining region 1 (LCDR1) of SEQ ID NO 23, a light chain complementarity determining region 2 (LCDR2) of SEQ ID NO 43, a light chain complementarity determining region 3 (LCDR3) of SEQ ID NO 63, a heavy chain complementarity determining region 1 (HCDR1) of SEQ ID NO 28, a heavy chain complementarity determining region 2 (HCDR2) of SEQ ID NO 48, and a heavy chain complementarity determining region 3 (HCDR3) of SEQ ID NO 68; an antibody comprising a light chain complementarity determining region 1 (LCDR1) of SEQ ID NO 24, a light chain complementarity determining region 2 (LCDR2) of SEQ ID NO 44, a light chain complementarity determining region 3 (LCDR3) of SEQ ID NO 64, a heavy chain complementarity determining region 1 (HCDR1) of SEQ ID NO 29, a heavy chain complementarity determining region 2 (HCDR2) of SEQ ID NO 49, and a heavy chain complementarity determining region 3 (HCDR3) of SEQ ID NO 69; or an antibody comprising a light chain complementarity determining region 1 (LCDR1) of SEQ ID NO 25, a light chain complementarity determining region 2 (LCDR2) of SEQ ID NO 45, a light chain complementarity determining region 3 (LCDR3) of SEQ ID NO 65, a heavy chain complementarity determining region 1 (HCDR1) of SEQ ID NO 30, a heavy chain complementarity determining region 2 (HCDR2) of SEQ ID NO 50, and a heavy chain complementarity determining region 3 (HCDR3) of SEQ ID NO 70.

In one example, the amino acid sequences of antibody clones (Ab6-10) which binds to Gn envelope glycoprotein of the present invention are shown in the following Tables 9-16.

Amino acid sequences of light chains and heavy chains binding to Gn envelope glycoprotein.

TABLE 9

| SEQ ID NO | Antibody and site | Sequence |
|---|---|---|
| 81 | light chain of Ab6 | ELALTQPPSVSVAPGKTAKITC GGDDIGSKTVQ WYQQTSGQAPVLVVY DDSDRPS GIPERFSGANSGNTATLTISRVEAGDEADYYC QVWDGRSDHVV FGGGTKLTVL |
| 82 | light chain of Ab7 | ELVLTQPPSVSAAPGQKVTISC SGSSSNIGNNVVS WYQQLPGTAPKLLIY DDNRRPS GIPDRFSGSKSGTSATLDITGLQTGDEADYYC ATWDGSLTAGRVL FGSGTKLTVL |
| 83 | light chain of Ab8 | ELALTQPPSVSVAPAMTAKITC GGDDIGSTTVQ WYQQTSGQAPVLVVY DDSDRPS GIPERFSGANSGNTATLTISRVEAGDEADYYC QVWDGRSDHVV FGGGTKLTVL |
| 84 | light chain of Ab9 | ELELTQPPSVSGTPGKRVSMSC SGSRSNIGGNVVN WYQQLPGKAPKLFIY NNDQRPS GVPDRVSGSKSGTSVSVAISGLQPEDEADYYC AAWDDILNGVV FGGGTQLTVL |
| 85 | light chain of Ab10 | ELVMTQSPSSLSASVGDTVTITC RASQSIYTYLN WYHQTPGKAPKLLIS AASSLQS GVPSRFSGSGSGTDFTLTISSLQPEDFATYYC QQYADVPVT FGGGTKLEIK |
| 86 | heavy chain of Ab6 | QVQLVQSGAEVKKPGESLKISCKGS GYIFTNYWIG WVRQMPGKGLEWM GIIYPGDSDTRYSPSFQG QVTISADRSISTAYLQWSSLKASDTAMYYCA RLKLRGFSGGYGSGRRYFDYWG QGTLVTVSS |
| 87 | heavy chain of Ab7 | QVQLVQSGAEVKKPGESLKISCKGS GYSFTSYWIG WVRQMPGKGLEWM GIIYPGDSDTRYSPSFQG QVTISADKSISTAYLQWSSLKASDTAMYYCA RLKLRGFSGGYGSGSRYFDYWG QGTLVTVSS |
| 88 | heavy chain of Ab8 | QVQLVQSGAEVKKPGESLKISCKGS GYIFTNYWIG WVRQMPGKGLEWM GIIYPGDSDTRYSPSFQG QVTISADRSISTANLQWSSLKASDTALYYCA RLKLRGFSGGYGSGRRYFDYWG QGTLVTVSS |
| 89 | heavy chain of Ab9 | QVQLVQSGAEVKKPGESLKISCKGS GYNFTNYWIG WVRQLPGKGLEWM GIIYPGDSDTRYSPSFQG QVTISADKSISTAYLQWSSLKASDTAMYYCA RIRVIGFYD-- SSPPPLFDYWG QGTLVTVSS |
| 90 | heavy chain of Ab10 | EVQLVESGGGVVQPGRSLRLSCAAS GFTFSGYGIH WVRQAPGKGLEWV ALISYDGSNKYYADSVKG RFTISRDNSKNTLYLQMNSLRAEDTAVYYCA KDR-----DYFGSG-- FFDYWG QGTLVTVSS |

Amino acid sequences of light chain or heavy chain framework region 1 (LFR1 or HFR1) of the antibody binding to Gn envelope glycoprotein.

TABLE 10

| SEQ ID NO | Antibody and site | Sequence |
|---|---|---|
| 91 | LFR1 of Ab6 | ELALTQPPSVSVAPGKTAKITC |
| 92 | LFR1 of Ab7 | ELVLTQPPSVSAAPGQKVTISC |

TABLE 10-continued

| SEQ ID NO | Antibody and site | Sequence |
|---|---|---|
| 93 | LFR1 of Ab8 | ELALTQPPSVSVAPAMTAKITC |
| 94 | LFR1 of Ab9 | ELELTQPPSVSGTPGKRVSMSC |
| 95 | LFR1 of Ab10 | ELVMTQSPSSLSASVGDTVTITC |
| 96 | HFR1 of Ab6 | QVQLVQSGAEVKKPGESLKISCKGS |
| 97 | HFR1 of Ab7 | QVQLVQSGAEVKKPGESLKISCKGS |
| 98 | HFR1 of Ab8 | QVQLVQSGAEVKKPGESLKISCKGS |
| 99 | HFR1 of Ab9 | QVQLVQSGAEVKKPGESLKISCKGS |
| 100 | HFR1 of Ab10 | EVQLVESGGGVVQPGRSLRLSCAAS |

Amino acid sequences of light chain or heavy chain complementarity determining region 1 (LCDR1 or HCDR1) of the antibody binding to Gn envelope glycoprotein.

TABLE 11

| SEQ ID NO | Antibody and site | Sequence |
|---|---|---|
| 101 | LCDR1 of Ab6 | GGDDIGSKTVQ |
| 102 | LCDR1 of Ab7 | SGSSSNIGNNVVS |
| 103 | LCDR1 of Ab8 | GGDDIGSTTVQ |
| 104 | LCDR1 of Ab9 | SGSRSNIGGNVVN |
| 105 | LCDR1 of Ab10 | RASQSIYTYLN |
| 106 | HCDR1 of Ab6 | GYIFTNYWIG |
| 107 | HCDR1 of Ab7 | GYSFTSYWIG |
| 108 | HCDR1 of Ab8 | GYIFTNYWIG |
| 109 | HCDR1 of Ab9 | GYNFTNYWIG |
| 110 | HCDR1 of Ab10 | GFTFSGYGIH |

Amino acid sequences of light chain or heavy chain framework region 2 (LFR2 or HFR2) of the antibody binding to Gn envelope glycoprotein.

TABLE 12

| SEQ ID NO | Antibody and site | Sequence |
|---|---|---|
| 111 | LFR2 of Ab6 | WYQQTSGQAPVLVVY |
| 112 | LFR2 of Ab7 | WYQQLPGTAPKLLIY |
| 113 | LFR2 of Ab8 | WYQQTSGQAPVLVVY |
| 114 | LFR2 of Ab9 | WYQQLPGKAPKLFIY |
| 115 | LFR2 of Ab10 | WYHQTPGKAPKLLIS |
| 116 | HFR2 of Ab6 | WVRQMPGKGLEWM |
| 117 | HFR2 of Ab7 | WVRQMPGKGLEWM |
| 118 | HFR2 of Ab8 | WVRQMPGKGLEWM |

TABLE 12-continued

| SEQ ID NO | Antibody and site | Sequence |
|---|---|---|
| 119 | HFR2 of Ab9 | WVRQLPGKGLEWM |
| 120 | HFR2 of Ab10 | WVRQAPGKGLEWV |

Amino acid sequences of light chain or heavy chain complementarity determining region 2 (LCDR2 or HCDR2) of the antibody binding to Gn envelope glycoprotein.

TABLE 13

| SEQ ID NO | Antibody and site | Sequence |
|---|---|---|
| 121 | LCDR2 of Ab6 | DDSDRPS |
| 122 | LCDR2 of Ab7 | DDNRRPS |
| 123 | LCDR2 of Ab8 | DDSDRPS |
| 124 | LCDR2 of Ab9 | NNDQRPS |
| 125 | LCDR2 of Ab10 | AASSLQS |
| 126 | HCDR2 of Ab6 | GIIYPGDSDTRYSPSFQG |
| 127 | HCDR2 of Ab7 | GIIYPGDSDTRYSPSFQG |
| 128 | HCDR2 of Ab8 | GIIYPGDSDTRYSPSFQG |
| 129 | HCDR2 of Ab9 | GIIYPGDSDTRYSPSFQG |
| 130 | HCDR2 of Ab10 | ALISYDGSNKYYADSVKG |

Amino acid sequences of light chain or heavy chain framework region 3 (LFR3 or HFR3) of the antibody binding to Gn envelope glycoprotein.

TABLE 14

| SEQ ID NO | Antibody and site | Sequence |
|---|---|---|
| 131 | LFR3 of Ab6 | GIPERFSGANSGNTATLTISRVEAGDEADYYC |
| 132 | LFR3 of Ab7 | GIPDRFSGSKSGTSATLDITGLQTGDEADYYC |
| 133 | LFR3 of Ab8 | GIPERFSGANSGNTATLTISRVEAGDEADYYC |
| 134 | LFR3 of Ab9 | GVPDRVSGSKSGTSVSVAISGLQPEDEADYYC |
| 135 | LFR3 of Ab10 | GVPSRFSGSGSGTDFTLTISSLQPEDFATYYC |
| 136 | HFR3 of Ab6 | QVTISADRSISTAYLQWSSLKASDTAMYYCA |
| 137 | HFR3 of Ab7 | QVTISADKSISTAYLQWSSLKASDTAMYYCA |
| 138 | HFR3 of Ab8 | QVTISADRSISTANLQWSSLKASDTALYYCA |
| 139 | HFR3 of Ab9 | QVTISADKSISTAYLQWSSLKASDTAMYYCA |
| 140 | HFR3 of Ab10 | RFTISRDNSKNTLYLQMNSLRAEDTAVYYCA |

Amino acid sequences of light chain or heavy chain complementarity determining region 3 (LCDR3 or HCDR3) of the antibody binding to Gn envelope glycoprotein.

TABLE 15

| SEQ ID NO | Antibody and site | Sequence |
|---|---|---|
| 141 | LCDR3 of Ab6 | QVWDGRSDHVV |
| 142 | LCDR3 of Ab7 | ATWDGSLTAGRVL |
| 143 | LCDR3 of Ab8 | QVWDGRSDHVV |
| 144 | LCDR3 of Ab9 | AAWDDILNGVV |
| 145 | LCDR3 of Ab10 | QQYADVPVT |
| 146 | HCDR3 of Ab6 | RLKLRGFSGGYGSGRRYFDYWG |
| 147 | HCDR3 of Ab7 | RLKLRGFSGGYGSGSRYFDYWG |
| 148 | HCDR3 of Ab8 | RLKLRGFSGGYGSGRRYFDYWG |
| 149 | HCDR3 of Ab9 | RIRVIGFYD--SSPPPLFDYWG |
| 150 | HCDR3 of Ab10 | KDR-----DYFGSG--FFDYWG |

Amino acid sequences of light chain or heavy chain framework region 4 (LFR4 or HFR4) of the antibody binding to Gn envelope glycoprotein.

TABLE 16

| SEQ ID NO | Antibody and site | Sequence |
|---|---|---|
| 151 | LFR4 of Ab6 | FGGGTKLTVL |
| 152 | LFR4 of Ab7 | FGSGTKLTVL |
| 153 | LFR4 of Ab8 | FGGGTKLTVL |
| 154 | LFR4 of Ab9 | FGGGTQLTVL |
| 155 | LFR4 of Ab10 | FGGGTKLEIK |
| 156 | HFR4 of Ab6 | QGTLVTVSS |
| 157 | HFR4 of Ab7 | QGTLVTVSS |
| 158 | HFR4 of Ab8 | QGTLVTVSS |
| 159 | HFR4 of Ab9 | QGTLVTVSS |
| 160 | HFR4 of Ab10 | QGTLVTVSS |

In one exemplary embodiment, the antibody which specifically binds to the envelope glycoprotein of SFTSV, Gn of the present invention may comprise a light chain comprising any one of amino acid sequences selected from the group consisting of SEQ ID NO 81, 82, 83, 84 and 85, and a heavy chain comprising any one of amino acid sequences selected from the group consisting of SEQ ID NO 86, 87, 88, 89 and 90. The antibody consisting of these specific sequences can specifically and effectively bind to the envelope glycoprotein, Gn, and thus can be very usefully used for detection of SFTSV.

In another exemplary embodiment, preferably, the antibody which specifically binds to the envelope glycoprotein of SFTSV, Gn of the present invention can be provided as an antibody comprising a light chain comprising an amino acid sequence of SEQ ID NO 81 and a heavy chain comprising an amino acid of SEQ ID NO 86, an antibody comprising a light chain comprising an amino acid sequence of SEQ ID NO 82 and a heavy chain comprising an amino acid of SEQ ID NO 87, an antibody comprising a light chain comprising an amino acid sequence of SEQ ID NO 83 and a heavy chain comprising an amino acid of SEQ ID NO 88, an antibody comprising a light chain comprising an amino acid sequence of SEQ ID NO 84 and a heavy chain comprising an amino acid of SEQ ID NO 89, and an antibody comprising a light chain comprising an amino acid sequence of SEQ ID NO 85 and a heavy chain comprising an amino acid of SEQ ID NO 90.

In another exemplary embodiment, the antibody which specifically binds to the envelope glycoprotein of SFTSV, Gn of the present invention can comprise a light chain complementarity determining region 1 (LCDR1) comprising any one of amino acid sequences selected from the group consisting of SEQ ID NOs 101, 102, 103, 104 and 105, a light chain complementarity determining region 2 (LCDR2) comprising any one of amino acid sequences selected from the group consisting of SEQ ID NOs 121, 122, 123, 124 and 125, a light chain complementarity determining region 3 (LCDR3) comprising any one of amino acid sequences selected from the group consisting of SEQ ID NOs 141, 142, 143, 144 and 145, a heavy chain complementarity determining region 1 (HCDR1) comprising any one of amino acid sequences selected from the group consisting of SEQ ID NOs 106, 107, 108, 109 and 110, a heavy chain complementarity determining region 2 (HCDR2) comprising any one of amino acid sequences selected from the group consisting of SEQ ID NOs 126, 127, 128, 129 and 130, and a heavy chain complementarity determining region 3 (HCDR3) comprising any one of amino acid sequences selected from the group consisting of SEQ ID NOs 146, 147, 148, 149 and 150.

In another exemplary embodiment, the antibody which specifically binds to the envelope glycoprotein of SFTSV, Gn of the present invention can be provided as an antibody comprising a light chain complementarity determining region 1 (LCDR1) of SEQ ID NO 101, a light chain complementarity determining region 2 (LCDR2) of SEQ ID NO 121, a light chain complementarity determining region 3 (LCDR3) of SEQ ID NO 141, a heavy chain complementarity determining region 1 (HCDR1) of SEQ ID NO 106, a heavy chain complementarity determining region 2 (HCDR2) of SEQ ID NO 126, and a heavy chain complementarity determining region 3 (HCDR3) of SEQ ID NO 146; an antibody comprising a light chain complementarity determining region 1 (LCDR1) of SEQ ID NO 102, a light chain complementarity determining region 2 (LCDR2) of SEQ ID NO 122, a light chain complementarity determining region 3 (LCDR3) of SEQ ID NO 142, a heavy chain complementarity determining region 1 (HCDR1) of SEQ ID NO 107, a heavy chain complementarity determining region 2 (HCDR2) of SEQ ID NO 127, and a heavy chain complementarity determining region 3 (HCDR3) of SEQ ID NO 147; an antibody comprising a light chain complementarity determining region 1 (LCDR1) of SEQ ID NO 103, a light chain complementarity determining region 2 (LCDR2) of SEQ ID NO 123, a light chain complementarity determining region 3 (LCDR3) of SEQ ID NO 143, a heavy chain complementarity determining region 1 (HCDR1) of SEQ ID NO 108, a heavy chain complementarity determining region 2 (HCDR2) of SEQ ID NO 128, and a heavy chain complementarity determining region 3 (HCDR3) of SEQ ID NO 148; an antibody comprising a light chain complementarity determining region 1 (LCDR1) of SEQ ID NO 104, a light chain complementarity determining region 2 (LCDR2) of SEQ ID NO 124, a light chain complementarity determining region 3 (LCDR3) of SEQ ID NO 144, a heavy chain complementarity determining region 1 (HCDR1) of SEQ ID NO 109, a heavy chain complementarity determining region 2 (HCDR2) of SEQ ID NO 129, and a heavy chain complementarity determining region 3 (HCDR3) of SEQ ID NO 149; or an antibody comprising a light chain complementarity determining region 1 (LCDR1) of SEQ ID NO 105, a light chain complementarity determining region 2 (LCDR2) of SEQ ID NO 125, a light chain complementarity determining region 3 (LCDR3) of SEQ ID NO 145, a heavy chain complementarity determining region 1 (HCDR1) of SEQ ID NO 110, a heavy chain complementarity determining region 2 (HCDR2) of SEQ ID NO 130, and a heavy chain complementarity determining region 3 (HCDR3) of SEQ ID NO 150.

In one exemplary embodiment, the antibody of the present invention may include an antibody comprising an amino acid which is a homologue of an antibody comprising heavy chains and light chains described in the above Table 1 or Table 9. In addition, the antibody of the present invention may comprise a light chain variable region comprising the LCDR1, LCDR2 and LCDR3 sequences, and a heavy chain variable region comprising HCDR1, HCDR2 and HCDR3 sequences, and at least one of these CDR sequences may have the antibody disclosed herein or a specific amino acid sequence based on its conservative modification. In addition, the antibody of the present invention may be an antibody possessing functional properties of antibody binding to the envelope glycoprotein of SFTSV, Gc or Gn, and may be an antibody which binds to a same epitope as an antibody comprising heavy chains and light chains disclosed in Table 1 or Table 9. Furthermore, the antibody of the present invention may be prepared using an antibody having one or more kinds of light chains or antibody sequences suggested herein as a starting material for engineering the modified antibody, and comprise all the antibodies having partially modified properties from the starting antibody.

In the present invention, the antibody may comprise a modification to the framework region in the light chain or heavy chain in order to improve properties of the antibody. In addition, the antibody may have at least $1\times10^7 M^{-1}$, $1\times10^8 M^{-1}$, $1\times10^9 M^{-1}$, $1\times10^{10}$ $M^{-1}$ or $1\times10^{11} M^{-1}$ of affinity constant (KA) for the envelope glycoprotein of SFTSV.

In addition, the antibody of the present invention may be a complete human antibody which specifically binds to the SFTSV envelope glycoprotein. This can have further reduced antigenicity when administered into a human subject, compared with chimera antibody, etc. The human antibody may comprise a heavy chain or light chain variable region, or a full length of heavy chain or light chain that are products of or one derived from a specific germline sequence, when it is collected from a system using a variable region or full length chain human germline immunoglobulin gene. Moreover, the antibody of the present invention may be a De-immunized antibody having antigenicity.

In addition, in the present invention, the antigen may be a bispecific or a multispecific antibody. The antibody or its antigen-binding fragment of the present invention may be a bispecific molecule binding to two or more of different binding sites or target molecules.

In some exemplary embodiments, the antibody of the present invention may be a monoclonal antibody which specifically binds to the envelope glycoprotein of SFTSV. For example, the antibody of the present invention may be a human or humanized monoclonal antibody or chimera antibody which specifically binds to the envelope glycoprotein of SFTSV, and the antibody of the present invention may comprise a human heavy chain constant region and a human light chain constant region. In addition, the antibody of the present invention may be a single chain antibody, and the antibody of the present invention may be a Fab fragment, and may be a scFv (Single-chain variable fragment), and may be an IgG isotype. Preferably, the antibody of the present invention may be the scFv.

In the present invention, the monoclonal antibody may be produced by common monoclonal antibody methods, and the synthesized antibody genes can be expressed and purified by inserting them into a vector for antibody expression, preferably pcDNA, pCI, pCMV or pCEP4. In addition, viral or carcinogenic transformation of B lymphocytes may be used, and it may be prepared on the basis of the sequence of murine monoclonal antibody prepared using a murine system. For example, using a standard molecule biology technology, a DNA encoding heavy chain and light chain immunoglobulins is obtained from a murine hybridoma, and a non-murine immunoglobulin sequence can be contained with it.

In some exemplary embodiments, the present invention provides an antibody comprising a framework in which an amino acid is substituted with an antibody framework from each human VH or VL germline sequence, or its antigen binding fragment.

In another exemplary embodiment, the present invention provides a nucleic acid comprising a nucleotide sequence encoding a polypeptide comprising a light chain comprising any one of amino acid sequences selected from the group consisting of SEQ ID NOs 1, 2, 3, 4 and 5, and a polypeptide comprising a heavy chain comprising any one of amino acid sequences selected from the group consisting of SEQ ID NOs 6, 7, 8, 9 and 10. In one embodiment, the nucleic acid may be any one of nucleic acid sequences selected from the group consisting of SEQ ID NOs 161, 162, 163, 164, 165, 166, 167, 168, 169 and 170, and this is shown in the following Table 17 (The bolded parts are light chain variable regions (VL), and the underlined parts are heavy chain variable regions (VH)).

TABLE 17

| SEQ ID NO | Antibody | Nucleic acid sequence |
|---|---|---|
| 161 | Ab1 scFv | GAGCTCACACTCACGCAGTCTCCAGCCACCCTGTCTTTG TCTCCAGGGAAACAGCCACCCTCTCCTGCGGGGCCAGT CAGAGTGTTAGCACCAACTACTTAGCCTGGTACCAGCAG AAACCTGGCCTGGCGCCCAGGCTCCTCATCTATGATGCA TCCAGCAGGGCCACTGGCATCCCAGACAGGTTCAGTGGC AGTGGGTCTGGGACAGACTTCACTCTCACCATCAGCAGA CTGGCGCCTGAAGATTCTGCGGTGTATTACTGTCAGCAA TATGGTAGCTCACCTCTCACTTTCGGCGGAGGGACCAAG CTGGAGATCAAAGGTGGTTCCTCTAGATCTTCCTCCTCT GGTGGCGGTGGCTCGGGCGGTGGTGGGCAGGTGCAGCTG GTGCAGTCTGGGCCTGAGGTGAAGAAGCCTGGGTCCTCG GTGAAGGTCTCCTGCAAGGCTTCTGGAGGCACCTTCAGC ACCTATGCTATCAGCTGGGTGCGACAGGCCCCTGGACAA GGGCTTGAGTGGATGGGAGGGATCATCCCTATCTCTGGT ACAGCAAACTACGCACAGAAATTCCAGGGCAGAGTCACC ATTACCGCGGACGAATCCACGAGCACAGCCTACATGGAG CTGAGCAGCCTGAGATCTGAGGACACGGCCGTGTATTAC TGTGCGGTACCAGTAGTACCAGCTGCCAGCGGCCCTTTT GACTACTGGGGCCAGGGAACCCTGGTCACCGTCTCCTCA GCC |
| 162 | Ab2 scFv | GAGCTCGTGGTGACGCAGCCGCCCTCAGTGTCTGGGGCC CCAGGGCAGAGGGTCACCATCTCCTGTTCTGGAAGCAGC TCCAACATCGGAAATAATACTGTAAACTGGTACCAGCAG CTCCCAGGAACGGCCCCCAAACTCCTCATCTATAGTAAT AATCAGCGGCCCTCAGGGGTCCCTGACCGATTCTCTGGC TCCAAGTCTGGCACCTCAGCCTCCCTGGCCATCACTGGG CTCCAGGCTGACGATGAGGCTGATTATTACTGCCAGTCC TTTGACAGCAGCCTGAATGATTGGGTGTTCGGCGGGGGC ACCAAGCTGACCGTCCTAGGCGGTGGTTCCTCTAGATCT TCCTCCTCTGGTGGCGGTGGCTCGGGCGGTGGTGGGGAG GTGCAGCTGGTGGAGTCTGGGGGAGGCCTGGTCAAGCCT GGGGGGTCCCTGAGACTCTCCTGTGCAGCCTCTGGATTC ACCTTCAGTAGCTATAGCATGAACTGGGTCCGCCAGGCT CCAGGGAAGGGGCTGGAGTGGGTCTCATCCATTAGTAGT AGTAGTCGTTACATATTCTACGCAGACTCAGTGAAGGGC CGATTCACCATCTCCAGAGACAACGCCAAGAACTCACTG TATCTGCAAATGAACAGCCTGAGAGCCGAGGACACGGCT GTGTATTACTGTGCGAGCCTAGGATATTGTAGTGGTGGT AGCTGCTACGGGTTCCCGGAAGGTGGGAATGCTTTTGAT ATCTGGGGCCAAGGGACAATGGTCACCGTCTCTTCA |
| 163 | Ab3 scFv | GAGCTCGAGCTGACTCAGCCACCCTCAGTGTCTGGGGCC CCAGGGCAGAGGGTCACCATCTCCTGCACTGGGAGCAGC TCCAACATCGGGGCAGGTTATGATGTACACTGGTACCAG CAGCTTCCAGGAACAGCCCCCAAACTCCTCATCTATGGT AACAGCAATCGGCCCTCAGGGGTCCCTGACCGATTCTCT GGCTCCAAGTCTGACACCTCAGCCTCCCTGGCCATCAGT GGGCTCCGGTCCGAGGATGAGGCTGATTATTACTGTGCA GCATGGGATGACAGCCTGAATGGCCAGGTGGTATTCGGC GGAGGCACCAAGCTGACCGTCCTAGGCGGTGGTTCCTCT AGATCTTCCTCCTCTGGTGGCGGTGGCTCGGGCGGTGGT GGGCAGGTGCAGCTGCAGGAGTCGGGCCCAGGACTGGTG AAGCCTTCGGAGACCCTGTCCCTCACCTGCACTGTCTCT GGTGGGTCCTTCAGTGGTTACTACTGGAGCTGGATCCGC CAGCCCCCAGGAAAGGGGCTGGAGTGGATTGGGGAAATC ATTCATAGTGGAAGCACCAACTACAACCCGTCCCTCAAG AGTCGAGTCACCATATCAGTAGACACGTCCAAGAACCAA TTCTCCCTGAAGCTGAGCTCTGTGACCGCCGCGGACACG GCTGTGTATTACTGTGCGAGAGGTGATTATTATGATAGT AGTGGTGCCTTTGACTACTGGGGCCAGGGAACCCTGGTC ACCGTCTCCTCA |
| 164 | Ab4 scFv | GAGCTCGTGCTGACTCAGCCACCTTCAGCGTCTGGGACC CCCGGGCAGAGGGTCACCATCTCTTGTTCTGGAAGCAGC TCCAACATCGGAAGTAATACTGTAAACTGGTACCAGCAG CTCCCCGGAACGGCCCCCAAACTCCTCATCTATAGTAAT AATCAGCGGCCCCCAGGGGTCCCTGACCGATTCTCTGGC TCCAAGTCTGGCACCTCAGCCTCCCTGGCCATCAGTGGG CTCCAGTCTGAGGATGAGGCTGATTATTACTGCCAGTCC TATGACAGCAGCCTGAGTTATGTCTTCGGAACTGGCACC AAGGTGACCGTCCTAGGCGGTGGTTCCTCTAGATCTTCC TCCTCTGGTGGCGGTGGCTCGGGCGGTGGTGGGGAGGTG CAGCTGGTGGAGTCTGGGGGAGGCTTGGTACAGCCGGGG GGGTCCCTGAGACTCTCCTGTGCAGCCTCTGGATTCACC TTCAGTAGCTATAGCATGAACTGGGTCCGCCAGGCTCCA GGGAAGGGGCTGGAGTGGGTCTCATCCATTAGTAGTAGT AGTCGTTACATATTCTACGCAGACTCAGTGAAGGGCCGA TTCACCATCTCCAGAGACAACGCCAAGAACTCACTGTAT CTGCAAATGAACAGCCTGAGAGCCGAGGACACGGCTGTG TATTACTGTGCGAGCCTAGGATATTGTAGTGGTGGTAGC TGCTACGGGTTCCCGGAAGGTGGGAATGCTTTTGATATC TGGGGCCAAGGGACAATGGTCACCGTCTCTTCA |
| 165 | Ab5 scFv | GAGCTCGTGGTGACCCAGGAGCCCTCACTGACTGTGCCC CCAGGAGGGACAGTCACTCTCACCTGTGGCTCCAGCACT GGACCTGTCACCACTACTCAGTATCCCTACTGGTTCCAG CAGAAGCCTGCCAGGCCCCCAGGACACTCATTTATGAT ACCAACAACAGACACCCCTGGACACCTGCCCGCTTCTCA GGCTCCCTCCTTGGGGGCAAGGCTGCCCTGACCCTTTCG GGAGCGCAGCCTGAGGATGACGCTTAGTATTATTGCTTG CTCACCTCTGCTAGCGCTCCTTGGGTGTTCGGCGGAGGC ACCAAGCTGACCGTCCTAGGCGGTGGTTCCTCTAGATCT TCCTCCTCTGGTGGCGGTGGCTCGGGCGGTGGTGGGCAG GTGCAGCTGGTGCAGTCTGGGGGAGGCTTGGTCCAGCCT GGGGGGTCCCTGAGACTCTCCTGTTCAGCCTCTGGATTC ACCTTCAGTAGCTATGCTATGCACTGGGTCCGCCAGGCT CCAGGGAAGGGCTGGAATATGTTTCAGCTATTAGTAGT GATGGGGGTAGCACATATACGCAGACTCCGTGAAGGGC AGATTCACCATCTCCAGACAATTCCAAGACACGCTG TATCTTCAAATGAGCAGTCTGAGAGCTGAGGACACGGCT GTATATTACTGTGTGAACGATGGCAGCTCGAACCATTTT GACTACTGGGGCCAGGGAACCCTGGTCACCGTCTCCTCA |

TABLE 17-continued

| SEQ ID NO | Antibody | Nucleic acid sequence |
|---|---|---|

TABLE 17-continued

| SEQ ID NO | Antibody | Nucleic acid sequence |
|---|---|---|
| 166 | Ab6 scFv | GAGCTCGCCCTGACTCAGCCTCCCTCCGTGTCAGTGGCC CCAGGAAAGACGGCCAAGATTACCTGTGGGGGTGACGAC ATTGGAAGTAAAACTGTGCAATGGTACCAACAGACCTCA GGCCAGGCCCCTGTGCTGGTCGTCTATGACGATAGCGAC CGGCCCTCAGGGATCCCTGAGCGATTCTCCGCCAACTGC GCTGGGAACACGGCCACCCTGACCATCAGAGGGTCGCAA GCCGGGGATGAGGCCGACTATTACTGTCAGGTGTGGGAC GGCAGAAGTGATCATGTGGTTTTCGGCGGAGGGACCAAG CTGACCGTCCTAGGCGGTGGTTCCTCTAGATCTTCCTCC TCTGGTGGCGGTGGCTCGGGCGGTGGTGGGCAGGTGCAG CTGGTGCAGTCTGGAGCAGAGGTGAAAAAGCCCGGGGAG TCTCTGAAGATCTCCTGTAAGGGTTCTGGATACATCTTT ACCAACTACTGGATCGGCTGGGTGCGCCAGATGCCCGGG AAAGGCCTGGAGTGGATGGGGATCATCTATCCTGGTGAC TCTGATACCAGATACAGCCCGTCCTTCCAAGGCCAGGTC ACCATCTCAGCCGACAGGTCCATCAGCACCGCCTACCTG CAGTGGAGCAGCCTGAAGGCCTCGGACACCGCCATGTAT TACTGTGCGAGACTAAAGCTCCGGGGGTTTTCGGCGGC TATGGTTCAGGGAGACGCTACTTTGACTACTGGGGCCAG GGAACCCTGGTCACCGTCTCCTCA |
| 167 | Ab7 scFv | GAGCTCGTGCTGACGCAGCCGCCCTCAGTGTCTGCGGCC CCAGGACTGAAGGTCACCATCTCCTGCTCTGGAAGCAGC TCTAACATTGGGAATAATGTTGTATCCTGGTACCAGCAA CTCCCAGGAACAGCCCCCAAACTCCTCATTTATGACGAT AACCGGCGACCCTCAGGGATTCCTGACCGATTCTCTGGC TCCAAGTCTGGCACGTCAGCCACCCTGGACATCACCGGA CTCCAGACTGGGGACGAGGCCGATTACTACTGCGCAACA TGGGATGGCAGCCTGACTGCTGGCCGTGTGTTGTTCGGC AGTGGCACCAAGCTGACCGTCCTAGGTGGTGGTTCCTCT AGATCTTCCTCCTCTGGTGGCGGTGGCTCGGGCGGTGGT GGGCAGGTGCAGCTGGTGCAGTCTGGAGCAGAGGTGAAA AAGCCCGGGGAGTCTCTGAAGATCTCCTGTAAGGGTTCT GGATACAGCTTTACCAGCTACTGGATCGGCTGGGTGCGC CAGATGCCCGGGAAAGGCCTGGAGTGGATGGGGATCATC TATCCTGGTGACTCTGATACCAGATACAGCCCGTCCTTC CAAGGCCAGGTCACCATCTCAGCCGACAAGTCCATCAGC ACCGCCTACCTGCAGTGGAGCAGCCTGAAGGCCTCGGAC ACCGCCATGTATTACTGTGCGAGACTAAAGCTCCGGGGG TTTTCGGCGGCTATGGTTCAGGGAGCCGCTACTTTGAC TACTGGGGCCAGGGAACCCTGGTCACCGTCTCCTCA |
| 168 | Ab8 scFv | GAGCTCGCCCTGACTCAGCCTCCCTCCGTGTCAGTGGCC CCAGCAATGACGGCCAAGATTACCTGTGGGGGTGACGAC ATTGGAAGTACTACTGTGCAATGGTACCAACAGACCTCA GGCCAGGCCCCTGTGCTGGTCGTCTATGACGATAGCGAC CGGCCCTCAGGGATCCCTGAGCGATTCTCCGGCGCCAAC TCTGGGAACACGGCCACCCTGACCATCAGCAGGGTCGAA GCCGGGGATGAGGCCGACTATTACTGTCAGGTGTGGGAC GGCAGAAGTGATCATGTGGTTTTCGGCGGAGGGACCAAG CTGACCGTCCTAGGCGGTGGTTCCTCTAGATCTTCCTCC TCTGGTGGCGGTGGCTCGGGCGGTGGTGGGCAGGTGCAG CTGGTGCAGTCTGGAGCAGAGGTGAAAAAGCCCGGGGAG TCTCTGAAGATCTCCTGTAAGGGTTCTGGATACATCTTT ACCAACTACTGGATCGGCTGGGTGCGCCAGATGCCCGGG AAAGGCCTGGAGTGGATGGGGATCATCTATCCTGGTGAC TCTGATACCAGATACAGCCCGTCCTTCCAAGGCCAGGTC ACCATCTCAGCCGACAGGTCCATCAGCACCGCCAACCTG CAGTGGAGCAGCCTGAAGGCCTCGGACACCGCCCTGTAT TACTGTGCGAGACTAAAGCTCCGGGGGTTTTCGGCGGC TATGGTTCAGGGAGACGCTACTTTGACTACTGGGGCCAG GGAACCCTGGTCACCGTCTCCTCA |
| 169 | Ab9 scFv | GAGCTCGAGCTGACTCAGCCACCCTCAGTGTCTGGGACC CCCGGGAAGAGGGTCAGTATGTCTTGTTCTGGAAGTAGG TCCAACATCGGAGGTAATGTTGTGAACTGGTACCAGCAG CTCCCAGGAAAGGCCCCCAAACTCTTCATCTACAATAAT GATCAGCGGCCCTCAGGGGTCCCTGACCGAGTCTCTGGC TCCAAGTCAGGCACCTCAGTCTCCGTGGCCATCAGTGGG CTCCAGCCTGAAGATGAGGCTGATTATTACTGTGCAGCT TGGGATGACATCCTGAATGGTGTGGTCTTCGGCGGAGGG ACCCAGCTGACCGTCCTCGGCGGTGGTTCCTCTAGATCT TCCTCCTCTGGTGGCGGTGGCTCGGGCGGTGGTGGGCAG GTGCAGCTGGTGCAGTCTGGAGCAGAGGTGAAAAAGCCC GGGGAGTCTCTGAAGATCTCCTGTAAGGGTTCTGGATAC |

TABLE 17-continued

| SEQ ID NO | Antibody | Nucleic acid sequence |
|---|---|---|
| | | AACTTCACCAACTACTGGATCGGGTGGGTGCGCCAGCTG CCCGGGAAAGGCCTGGAGTGGATGGGGATCATCTATCCT GGTGACTCCGACACCAGATATAGCCCGTCCTTCCAAGGC CAGGTCACCATCTCAGCCGACAAGTCCATCAGCACCGCC TACCTGCAGTGGAGCAGCCTGAAGGCCTCGGACACCGCC ATGTATTACTGTGCGAGAATTCGAGTTATCGGATTCTAT GATAGTAGCCCCCCGCCCTTATTTGACTACTGGGGCCAG GGAACCCTGGTCACCGTCTCCTCA |
| 170 | Ab10 scFv | GAGCTCGTGATGACTCAGTCTCCATCTTCCCTGTCCGCA TCTGTGGGAGACACAGTCACCATCACTTGCCGGGCAAGT CAGAGCATTTACACCTATTTAAATTGGTATCACCAGACA CCAGGGAAAGCCCCTAAACTCCTGATTTCTGCTGCATCT AGTTTGCAAAGTGGTGTCCCATCAAGGTTCAGTGGCAGT GGGTCTGGGACAGATTTCACTCTCACCATCAGCAGTCTG CAACCTGAGGATTTTGCAACGTACTACTGTCAACAGTAT GCGGATGTCCCGGTCACTTTCGGCGGAGGGACCAAGCTG GAGATCAAAGGTGGTTCCTCTAGATCTTCCTCCTCTGGT GGCGGTGGCTCGGGCGGTGGTGGGGAGGTGCAGCTGGTG GAGTCTGGGGGAGGCGTGGTCCAGCCTGGGAGGTCCCTG AGACTCTCCTGTGCAGCCTCTGGATTCACCTTCAGTGGC TATGGCATACACTGGGTCCGCCAGGCTCCAGGCAAGGGG CTGGAGTGGGTGGCACTTATATCATATGATGGAAGTAAT AAATACTATGCAGACTCCGTGAAGGGCCGATTCACCATC TCCAGAGACAATTCCAAGAACACGCTGTATCTGCAAATG AACAGCCTGAGAGCTGAGGACACGGCTGTGTATTACTGT GCGAAAGATCGGGATTACTTTGGTTCAGGGTTCTTTGAC TACTGGGGCCAGGGAACCCTGGTCACCGTCTCCTCA |

In another exemplary embodiment, the antibody of the present invention may comprise an amino acid sequence having at least 90%, 95%, 97%, 98% or 99% sequence identity with any one of amino acid sequences disclosed in the above Tables 1-16, within the range that the antibody specificity to the envelope glycoprotein of SFTSV is maintained. In addition, a nucleic acid which can express the antibody of the present invention may comprise a nucleic acid having at least 90%, 95%, 97%, 98% or 99% sequence identity with any one of nucleic acid sequences disclosed in the above Table 17.

In addition, the present invention provides a vector and a host cell comprising the nucleic acid. The vector of the present invention may comprise a nucleic acid encoding an amino acid sequence of the antibody binding to the envelope glycoprotein of SFTSV, Gc, or a nucleic acid encoding an amino acid of the antibody binding to Gn. Otherwise, the vector of the present invention may express a bispecific antibody, by comprising all the two kinds of nucleic acids.

In one exemplary embodiment, the present invention provides (1) a first recombinant DNA fragment encoding a heavy chain of the antibody of the present invention, and (2) a second recombinant DNA fragment encoding a light chain of the antibody of the present invention. In another exemplary embodiment, the present invention provides a host cell comprising a recombinant DNA fragment encoding a heavy chain and a light chain of the present invention, respectively. In some exemplary embodiments, the antibody or its antigen binding fragment is a human monoclonal antibody or its antigen binding fragment.

To express a polynucleotide encoding the antibody binding to the envelope glycoprotein of SFTSV of the present invention, various expression vectors can be used. To produce an antibody in a mammalian host cell, both of virus-based or non-viral expression vector may be used. For example, vectors such as pcDNA, pCI, pCMV or pCEP4, and the like and host cells such as HEK293, CHO or CHO-DG44, and the like may be used.

The host cell possessing and expressing the antibody of the present invention may be a prokaryotic or eukaryotic cell. For example, the host cell may be *E. Coli*, preferably, *E. coli* ER2738. HB2151, BL21 and the like, and they may be useful for cloning and expressing the polynucleotide of the present invention. In addition, as other microbial hosts, *Bacillus*, for example, *Bacillus subtilis* or other intestinal bacteria, for example, *Salmonella* or *Serratia*, or various *Pseudomonas* species may be used. To express the antibody of the present invention, other microorganisms, for example, yeasts can be used, and an insect cell combined with a baculovirus vector may be also used.

In some preferable exemplary embodiments, a mammalian host cell may be used for expressing and preparing the SFTSV envelope glycoprotein binding polypeptide of the present invention. For example, it may be a hybridoma cell line expressing an endogenous immunoglobulin gene or a mammalian cell line possessing an exogenous expression vector. Further, it may comprise for example, CHO cell line, Cos cell line, HeLa cell, myeloma cell line, HEK cell line, transformed B-cell and hybridoma, as any animal or human cell. In addition, numerous appropriate host cell lines which can secret an immunoglobulin can be used, and preferably, HEK293, CHO or CHO-DG44 may be used.

In addition, the present invention provides a composition for diagnosing SFTSV comprising one or more kinds of SFTSV envelope glycoprotein binding molecules (for example, Gc or Gn binding antibody or its antigen binding fragment). The composition for diagnosis of the present invention may be usefully used for detection, isolation or purification of SFTSV. Moreover, the composition may further comprise one or more kinds of other agents appropriate for diagnosing SFTSV. In addition, the present invention provides a method for diagnosing SFTSV using the antibody of the present invention. The method may be used for quantitative or qualitative detection or diagnosis of SFTSV. Specifically, the diagnosis method may comprise a diagnosis examination to determine the expression of envelope glycoprotein and/or nucleic acid of SFTSV and the function of envelope glycoprotein of SFTSV from a biological sample (for example, blood, serum, cell or tissue) or a subject who is suffering from or at risk of developing SFTS. In the present invention, the detection includes quantitative and/or qualitative analysis, and includes detection of existence and absence and detection of virus titer, and this method has been known in the art, and those skilled in the art may select a proper method to conduct the present invention.

In the present invention, the detection of diagnosis or diagnosis of SFTSV may be detected by radio immunoassay, western blot, ELISA (Enzyme linked immunosorbent assay) or immune fluorescence assay, etc. which detects an antigen-antibody complex. In the present invention, an antigen may be labeled with a label such as a radioactive material, enzyme or fluorescent material, etc.

In one embodiment, the method of diagnosis of the present invention may use a complex in which the antibody to the envelope glycoprotein of SFTSV is conjugated to magnetic beads. Specifically, the method can more effectively detect, isolate or purify SFTSV, using the complex in which the antibody specific to the envelope glycoprotein of SFTSV, Gc or Gn is combined to magnetic beads. The antibody to the SFTSV envelope glycoprotein-magnetic bead complex combines with SFTSV existed in a subject using properties of the antibody and at that time, when the magnetic beads are pulled by magnetic power, viruses and other materials in the subject are separated, thereby effectively purifying the virus. The virus purified in this way is relatively useful for RNA isolation, as impurities are removed, and through this, purification result data of good quality can be obtained. In addition, an immunochemical response using another antibody can be processed for the virus attached to magnetic beads, and through this, SFTSV existed in the subject can be rapidly confirmed. The schematic figure of the diagnosis method was shown in FIG. 4.

In addition, the present invention provides a kit for diagnosing SFTSV comprising an antibody binding to an envelope glycoprotein of SFTSV. The kit may comprise any one or more aforementioned antibodies and a reagent for detecting an antigen-antibody complex. As the reagent for detecting an antigen-antibody complex, reagents used for radio immunoassay, ELISA (Enzyme linked immunosorbent assay) or immune fluorescence assay and the like may be used.

For example, for the detection of the immunoreaction, the detection reagent may be labeled directly or indirectly in the form of sandwich. In case of direct labeling method, a serum sample used for array, etc. may be labeled by a fluorescence label such as Cy3 or Cy5. In case of sandwich method, the detection may be performed by combining a target protein with a labeled detection antibody, after combining a non-labeled serum sample with an array in which a detection reagent is attached in advance. In case of sandwich method, as the sensitivity and specificity can be increased, the detection in the level of pg/mL is possible. Besides that, a radioactive material, a color material, a magnetic particle or a dense electron particle and the like may be used as a labeling material. A confocal microscope may be used for the fluorescence strength, and for example, may be obtained from Affymetrix, Inc. or Agilent Technologies, Inc, etc.

The kit of the present invention may further comprise one or more additional components needed for binding analysis, and for example, may further comprise a binding buffer, a reagent needed for sample preparation, a syringe for blood collection or negative and/or positive control. The kit of the present invention which can comprise various detection reagents may be provided for ELISA analysis, dip stick rapid kit analysis, microarray, gene amplification, or immunoassay, etc. according to analysis aspects, and proper detection reagents may be sorted according to the analysis aspects.

In addition, the present invention provides a pharmaceutical composition comprising the antibody binding to SFTSV envelope glycoprotein of the present invention. Preferably, the pharmaceutical composition may be used for prevention or treatment of SFTS. The antibody of the present invention can effectively prevent or treat SFTS, by neutralizing SFTSV and blocking proliferation of virus.

In the present invention, the composition may further contain one or more kinds of other agents appropriate for treating or preventing an SFTSV related disease. The carrier which can be used for the pharmaceutical composition may enhance the effect of composition, or stabilize the composition, or make preparation of the composition easy. The pharmaceutically acceptable carrier may comprise a physiologically acceptable solvent, a dispersive medium, a coating agent, an anti-bacterial agent, an anti-fungal agent, an isotonic agent or an absorption delaying agent and the like.

In the present invention, the pharmaceutical composition may be administered by a variety of methods known in the art, and the administration route and/or method may vary depending on the desired result. The pharmaceutical composition may be administered by administration methods, for example, intravenous, intramuscular, intraperitoneal or subcutaneous, and the like. According to the administration route, the active compound, antibody may be coated with a material protecting the compound from the action of acids and other natural conditions which may inactivate the compound.

In the present invention, the composition may be a sterile fluid. To maintain a proper fluidity, for example, a coating material such as lecithin or a surfactant may be used. In addition, the composition may comprise an isotonic agent (for example, sugar, polyalcohol, mannitol, sorbitol, and sodium chloride, etc.) or an absorption delaying agent (aluminum monostearate or gelatin, etc.).

In the present invention, the pharmaceutical composition may be prepared according to methods known in the art and commonly conducted, and preferably, may be prepared under GMP condition. The pharmaceutical composition may comprise a therapeutically effective dose or efficacious dose of the SFTSV envelope glycoprotein binding antibody. In addition, the dosage level of active ingredients in the pharmaceutical composition may be enough to achieve a therapeutic effect without toxicity to a patient.

In the present invention, the treatment dosage may be titrated to optimize safety and efficacy. When the antibody of the present invention is administered systemically, the range of dosage may be about 0.0001 to 100 mg, more commonly 0.01 to 15 mg per 1 kg of the host body weight. An exemplary treatment method entails systemic administration once per two weeks, or once per one month, or once per three months to 6 months. In some methods of systemic administration, the dosage is, and in some methods, the dosage may be adjusted to achieve the serum antibody concentration of 1 to 1000 μg/mL in some methods of systemic administration and 25 to 500 μg/mL in some methods. Otherwise, when less frequent administration is required, the antibody may be administered by a time-release agent. The dosage and frequency may be differed according to the half-life of the antibody in a patient. In prophylactic purposes, the relatively low dosage may be administered at relatively infrequent intervals for a long period of time.

In addition, the present invention provides a method for preventing or treating SFTS using the pharmaceutical composition. The prevention or treatment method may comprise administering the composition comprising the antibody of the present invention in an therapeutically effective amount. The "therapeutically effective amount" indicates an amount of the antibody of the present invention or the composition comprising thereof which is effective for prevention or treatment of SFTS diseases.

In addition, the present invention provides a use of an SFTSV envelope glycoprotein binding antibody for preparation of a composition for diagnosis of SFTSV. For the preparation of the composition for diagnosis, the antibody or composition comprising thereof of the present invention may comprise additional components such as an acceptable carrier, etc.

Furthermore, the present invention provides a use of an SFTSV envelope glycoprotein binding antibody. The antibody which specifically binds to SFTSV of the present invention may be used for SFTSV diagnosis, and may be used as a diagnosis use determining expression of the envelope glycoprotein and/or nucleic acid of SFTSV and the function of the protein from a subject who is suffering from or at risk of developing SFTS. In addition, the antibody of the present invention may be used as a use of prevention or treatment of SFTS occurred by SFTSV for a who is at risk of developing or suffering from SFTS.

Advantageous Effects

The antibody of the present invention can specifically bind to envelope glycoprotein of SFTSV, Gc or Gn, and thus SFTSV can be effectively detected or diagnosed and SFTS can be treated, using the antibody of the present invention.

BRIEF DESCRIPTION OF DRAWINGS

FIG. 1 shows the amino acid sequences of antibody clones Ab1 to Ab10.

Figure 4:
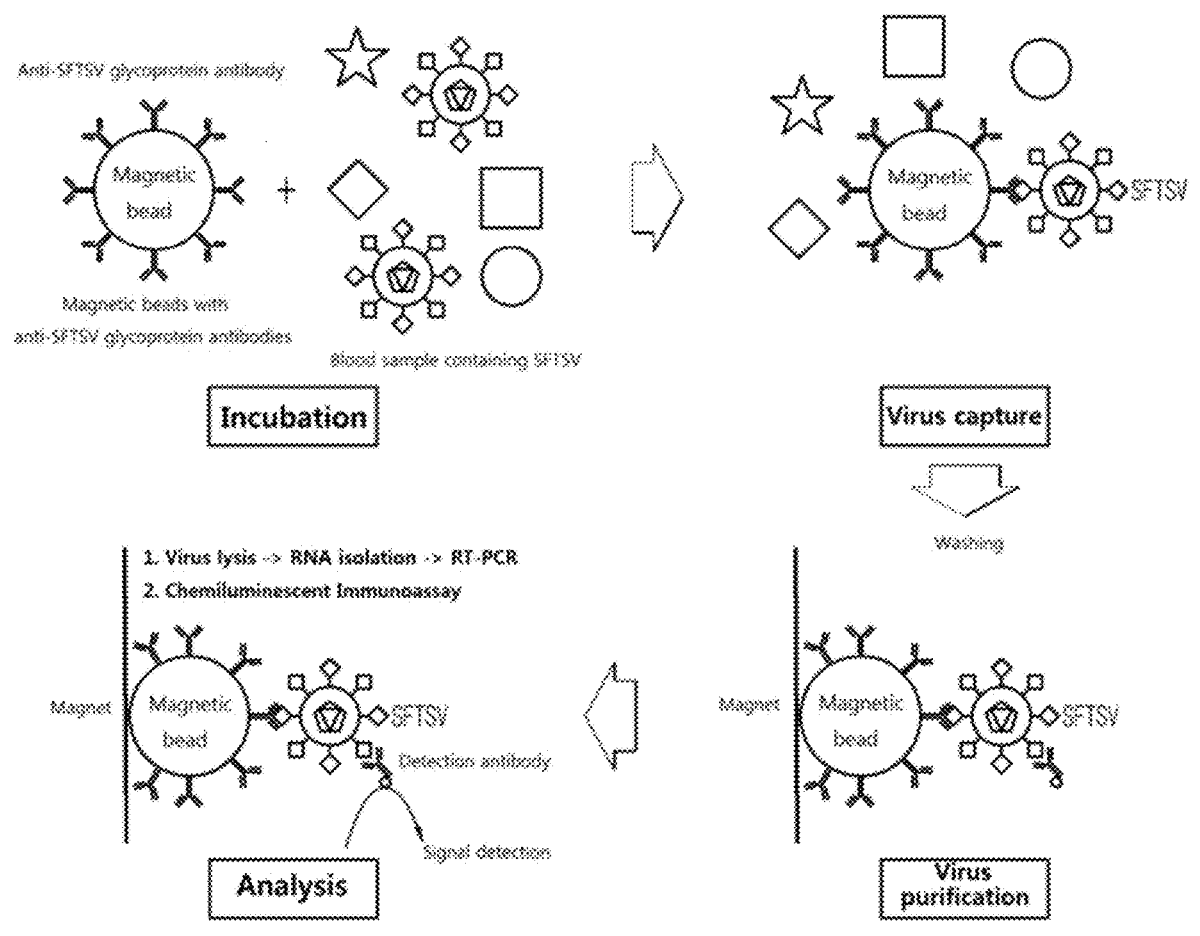

FIG. 4 is a schematic figure showing the method for detecting SFTSV using an antibody-magnetic bead complex.

DETAILED DESCRIPTION

Figure 2:
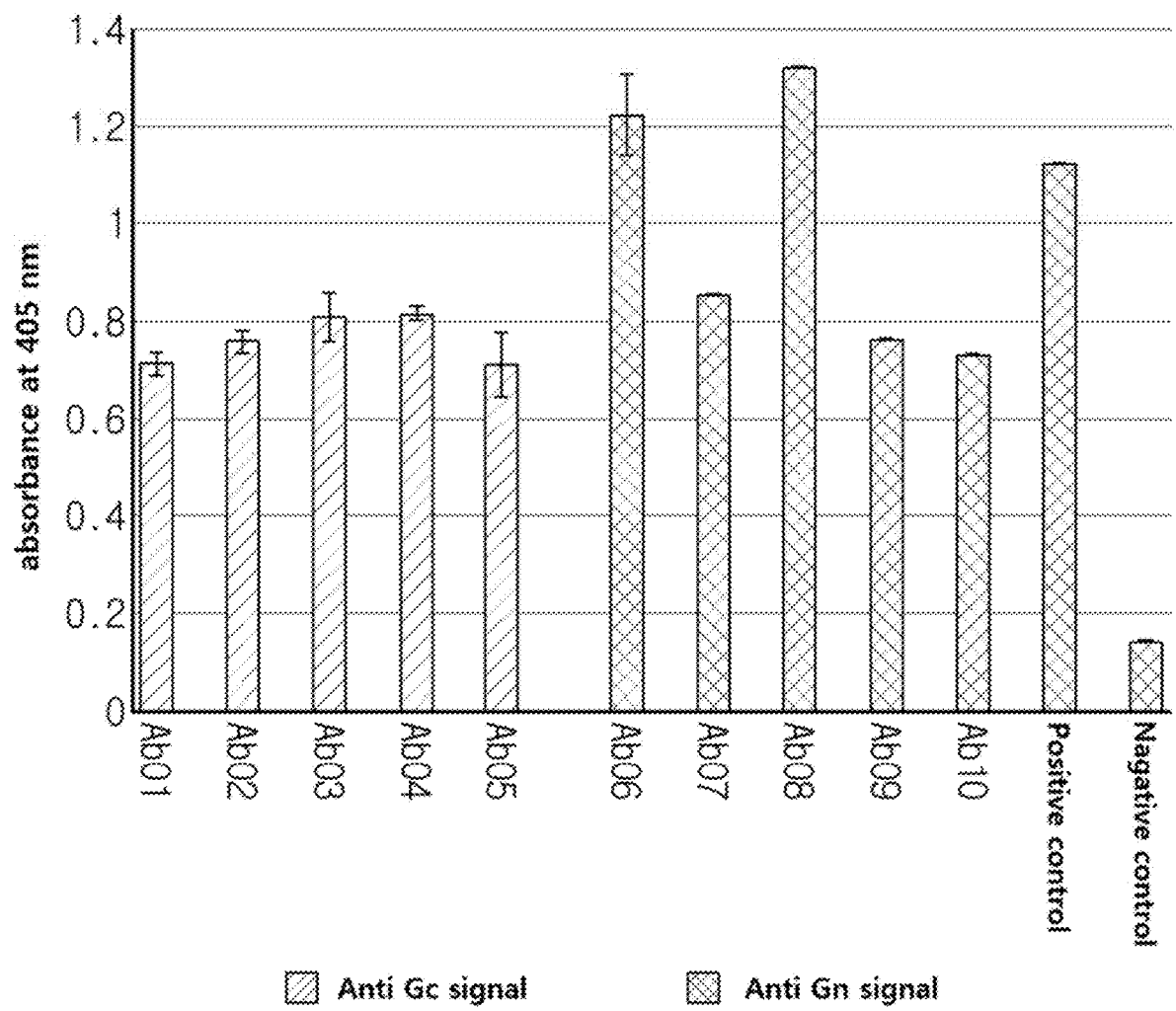
FIG. 2 shows the ELISA analysis result of scFv fragment antibody purified for SFTSV envelope glycoprotein Gc and Gn. These data show mean±S.D of 3 times repeated samples.

Hereinafter, examples, etc. will be described in detail to facilitate understanding of the present invention. However, the examples according to the present invention can be modified into various other forms, and the scope of the present invention should not be construed as being limited to the following examples. The examples of the present invention are provided to describe the present invention more completely to those skilled in the art.

Example 1: Preparation of Cells

Vero cells derived from African green monkey kidneys were purchased from Korean Cell Line Bank, and cultured at 37° C. under 5% carbon dioxide circumstance with Roswell Park Memorial Institute (RPMI)-1640 medium (Welgene) supplemented with 2% heat inactivated fetal bovine serum (Gibco) and penicillin-streptomycin (Gibco).

Example 2: Preparation of Virus Strains

The SFTS virus used in the present experiment was KF358691 which was isolated from a serum sample of 63-year-old female patient who was hospitalized in Seoul National University hospital and dead in 2012 [Kim K H, Yi J, Kim G, Choi S J, Jun K I, Kim N H, et al. Severe fever with thrombocytopenia syndrome, South Korea, 2012. *Emerging infectious diseases*. 2013; 19(11):1892-4.]. The isolated virus was inoculated into a single layer of Vero cells and cultured at 37° C. under 5% carbon dioxide circumstance. The virus was proliferated in Vero cells and all the experiments were performed at the third viral passage of virus culturing. Using Reed-Muench method, 50% tissue culture infection dose (TCID50) was titrated in Vero cells.

Example 3: Preparation of Recombinant SFTS Virus Glycoprotein and Single Chain Variable Fragment Antibody Fusion Protein The amino acid sequence of SFTS virus glycoprotein used in the present experiment was previously reported [Kim K H, Yi J, Kim G, Choi S J, Jun K I, Kim N H, et al. Severe fever with thrombocytopenia syndrome, South Korea, 2012. Emerging infectious diseases. 2013; 19(11):1892-4.]. To get a DNA strand encoding the SFTS virus glycoprotein, a human codon optimized DNA sequence corresponding to the amino acid sequence of SFTS virus glycoprotein of SEQ ID NO 171 (GenBank Accession No: AGT98506, amino acids 20-452 for Gn glycoprotein, amino acids 563-1035 for Gc glycoprotein) was synthesized (GenScript).

To overexpress recombinant SFTS virus glycoprotein Gc and Gn which were fused to human immunoglobulin G1 (IgG1) Fc region (Gc-Fc, Gn-Fc) or fused to human Ig k-chain constant region (Gc-Ck, Gn-Ck), the SFTS glycoprotein-encoding gene was prepared according to the method disclosed in [Park S, Lee D H, Park J G, Lee Y T, Chung J. A sensitive enzyme immunoassay for measuring cotinine in passive smokers. *Clinica chimica acta; international journal of clinical chemistry.* 2010; 411 (17-18):1238-42.], [Lee Y, Kim H, Chung J. An antibody reactive to the Gly63-Lys68 epitope of NT-proBNP exhibits O-glycosylation-independent binding. *Experimental & molecular medicine.* 2014; 46:e114.].

First of all, a DNA sequence obtained by amplifying the Fc region of human IgG1 using 2 kinds of primers (5'-GAGCCCAAATCTTGTGACAAAACTCAC-3') and (5'-GGATCCTCATTTACCCGGGGACAGGGAG-3') from human marrow-derived cDNA library (Clontech Laboratories), or the synthesized constant region of human Ig k-chain (UniProtKB/Swiss-Prot: P01834.1) was modified to be positioned at the DNA 3' side of gene sequence to be added. The gene sequence to be added was cloned in a modified pCEP4 vector (Invitrogen) to enable gene addition by SfiI restriction enzyme.

The antibody clone was produced in the form of single chain variable fragment-human IgG1 Fc region fusion protein (scFv-Fc) using scFv coding DNA of each clone. Then, the vector was transfected into HEK293F cell (Invitrogen) using polyethyleneimine (Polysciences), and the transfected cell was cultured in FreeStyle™ 293 expression medium containing 100 U/L penicillin-streptomycin. The overexpressed recombinant SFTS virus glycoprotein fusion protein was purified through an affinity chromatography using A/KappaSelect column and AKTA pure chromatography system (GE Healthcare).

Example 4: Antibody Library Construction and Biopanning

Peripheral blood monocytes of patient recovered from SFTS were collected using Ficoll-Paque solution (GE Healthcare). The total RNAs were separated using TRIzol reagent (Invitrogen), and cDNA was synthesized from the total RNAs using SuperScript III first strand cDNA synthesis kit with oligo(dT) priming. Using the cDNA, the phage-display library of human single chain variable fragment (scFv) was constructed using pComb3XSS phagemid vector. In addition, to select scFv clone from the library, as disclosed in [Barbas C F, Burton D R, Scott J K, Silverman G J. Phage display: a laboratory manual: CSHL Press; 2004.], 4 rounds of biopanning were performed. 3 µg of recombinant SFTS virus glycoprotein Gc or Gn human IgG1 Fc region fusion protein (Gc-Fc, Gn-Fc) was used for coating 5×106 of magnetic Dynabeads M-270 epoxy beads (Invitrogen) according to the manufacturer's instruction for each round of biopanning. And then the beads bound with proteins were used for biopanning procedures.

Example 5: Screening of Single Chain Variable Fragment Antibody to SFTS Virus To select an individual antibody clone which bound to SFTS virus glycoproteins, the phage clone was selected form the last round of biopanning, and scFv-display phage was prepared for phage enzyme immunoassay. Microtiter plate (Corning) was coated with 100 ng of recombinant Gc, Gn human Ig k-chain constant region fusion proteins (Gc-Ck, Gn-Ck) per well at 4° C. overnight. The well was blocked with 3% (w/v) BSA in 100 µl of PBS at 37° C. for 1 hour, and cultured with 50 µl of culture supernatant containing phage at 37° C. for 2 hours, and washed with 0.05% (v/v) Tween20 in 150 µl of PBS three times. Then, 50 ml of horseradish peroxidase (HRP)-bound anti-M13 antibody distilled in a blocking buffer (1:5000) was added to each well, and then the plate was cultured at 37° C. for 1 hour. After washing with 150 µl of 0.05% PBST, 50 µl of 2,2-azino-bis-3-ethylbenzothiazoline-6-sulfonic acid (ABTS) substrate solution (Pierce) was added to each well, and cultured at the room temperature for 30 minutes. And then the absorbance of each well was measured at 405 nm using a microplate reader (Labsystems).

Example 6: Neutralization Analysis

The SFTS virus specific scFv-Fc fusion antibody (100 µl/ml) was serially diluted to be decreased 10 folds each by 0.01 µl/ml. scFvs of each concentration was mixed in an equivalent volume of 100 TCID50 SFTS virus (strain KF358691) and cultured at 37° C. for 1 hours. Then, the virus-antibody mixture was transferred to the single layer of Vero cells in an 8-well confocal microscope chamber and cultured at 37° C. for 1 hour. After removing the virus-antibody mixture, samples were cultured in RPMI-1640 medium containing 2% FBS and antibiotics at 37° C. under 5% carbon dioxide circumstance. Vero cells in the 8-well confocal microscope chamber were used for immune fluorescence assay (IFA). All the experiments were performed three times and the relative neutralization effect was measured by comparing with MAb 4-5 [Xiling Guo et al. A human antibody neutralizing SFTS virus, an emerging hemorrhagic fever virus, 2013. Clin. Vaccine Immunol. 2013; 20(9):1426-32).] as a positive control and anti-newcastle disease virus (NDV) antibody as a negative control

Example 7: Immune Fluorescence Analysis (IFA) and Fluorescence Intensity Measurement The relative neutralization effect was measured using immune fluorescence assay (IFA). Cells with or without treatment with virus-antibody mixture having or not having Ab10, MAb 4-5 (positive control), anti-NDV (negative control) were cultured for 2 days. The cells were fixed with 4% paraformaldehyde in phosphate-buffer saline (PBS) for 1 hour. After blocking and penetrating slides with 0.1% triton X-100 in 1% fetal bovine serum (BSA), they were cultured together with anti-SFTS virus glycoprotein Gn clone Ab6 antibody (5 µl/ml) at 4° C. overnight. The cells were washed and cultured with fluorescein isothiocyanate (FITC)-bound anti-human IgG (Pierce) at the room temperature for 1 hour. 4',6-diamidino-2-phenylindole dihydrochloride (DAPI) was used for dying a nucleus. Samples were experimented with a confocal microscope (Leica, Buffalo Grove, Ill., USA). Fluorescence signal strength was measured using computer assisted Leica application suite advanced fluorescence (LAS AF). The microscope photographs were taken in 5 regions of each slide using ×10/0.3 lens, and 3 median values were used for analysis. DAPI signal was set with 405 nm blue diode laser and Alexa 488 was adjusted with an argon ion laser.

Example 8: Production of scFv Antibody to SFTS Virus

Figure 1:
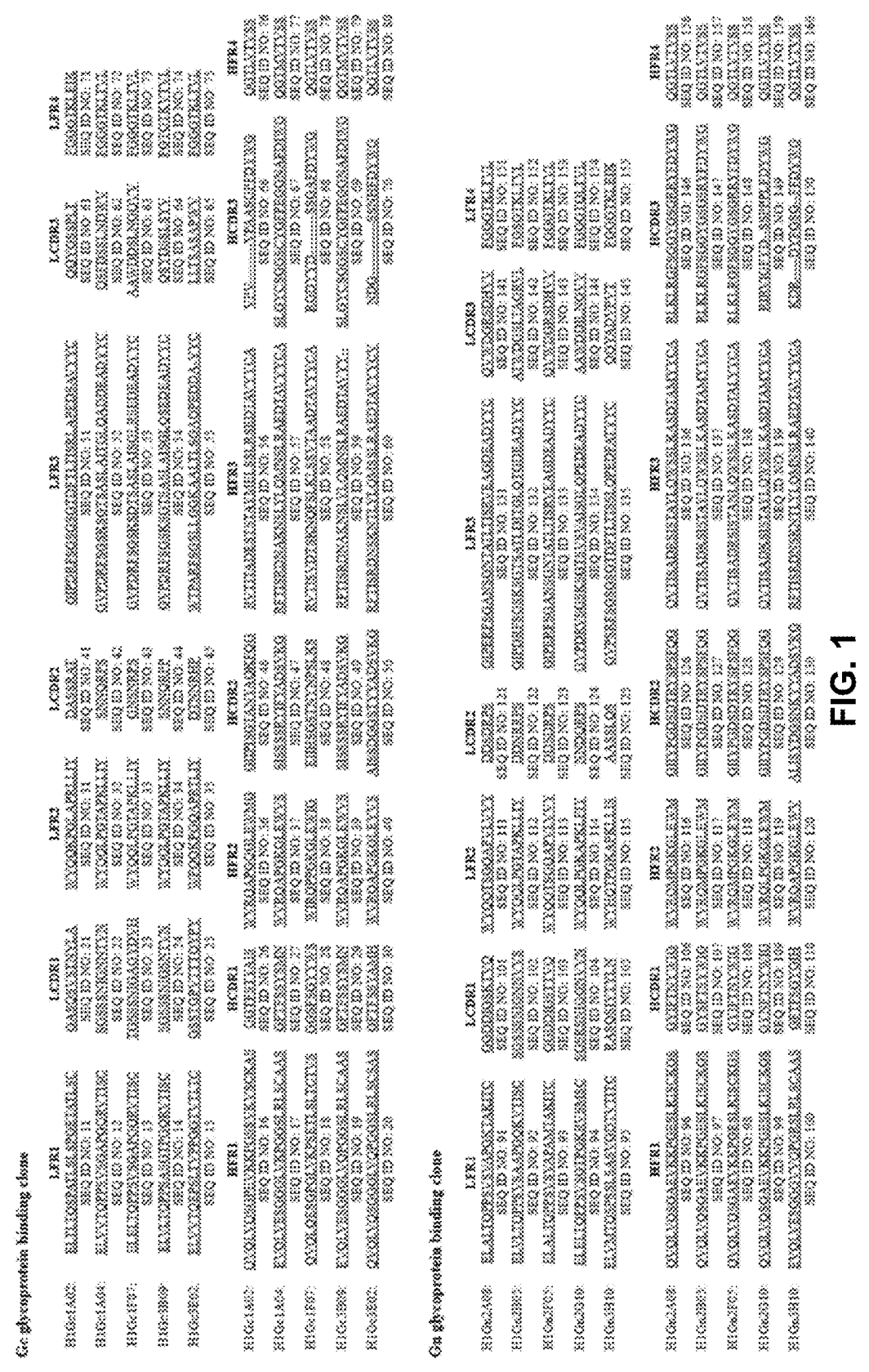

Human scFv library was biopanned for the recombinant SFTS virus glycoprotein. After 4 rounds of panning, the antibody clone was screened by enzyme-linked immunosorbent assay analysis (ELISA). It was shown that 10 clones (Ab1 to 5 for Gc and Ab6 to 10 for Gn) recognized the SFTS virus through ELISA. The ELISA analysis result was shown in FIG. 2, and the amino acid sequences of each antibody clone were shown in FIG. 1.

Example 9: Neutralization Activity of Antibody to SFTS Virus

Figure 3A:
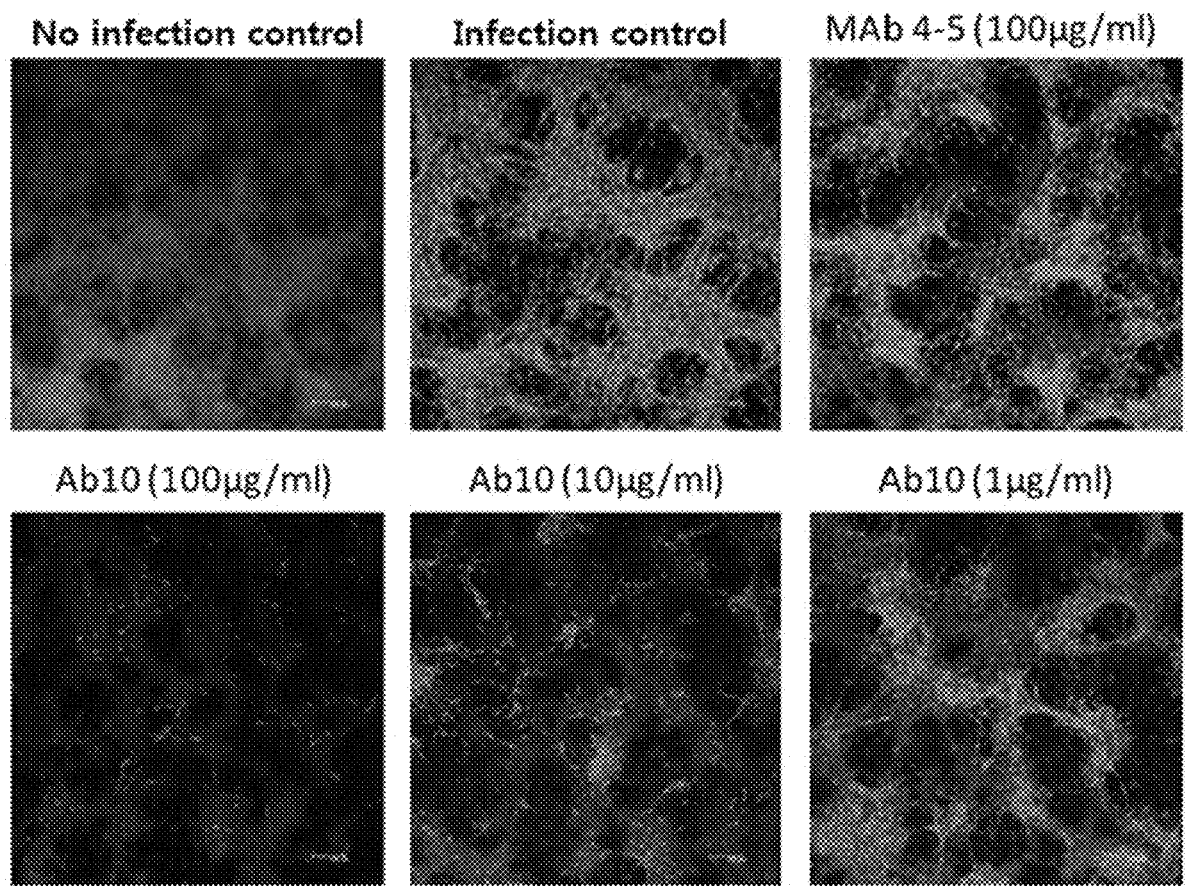
FIGS. 3A and 3B is (A) the immune fluorescence analysis result and (B) the fluorescence strength measurement of SFTSV infection. In the immune fluorescence analysis result, it was shown that Vero cells infected by SFTSV reacted with the antibody to Gn, and it was shown that Ab10 inhibited the virus infection dose-dependently. Ab10 was significantly excellent in inhibiting virus invasion compared with MAb 4-5.
Figure 3B:
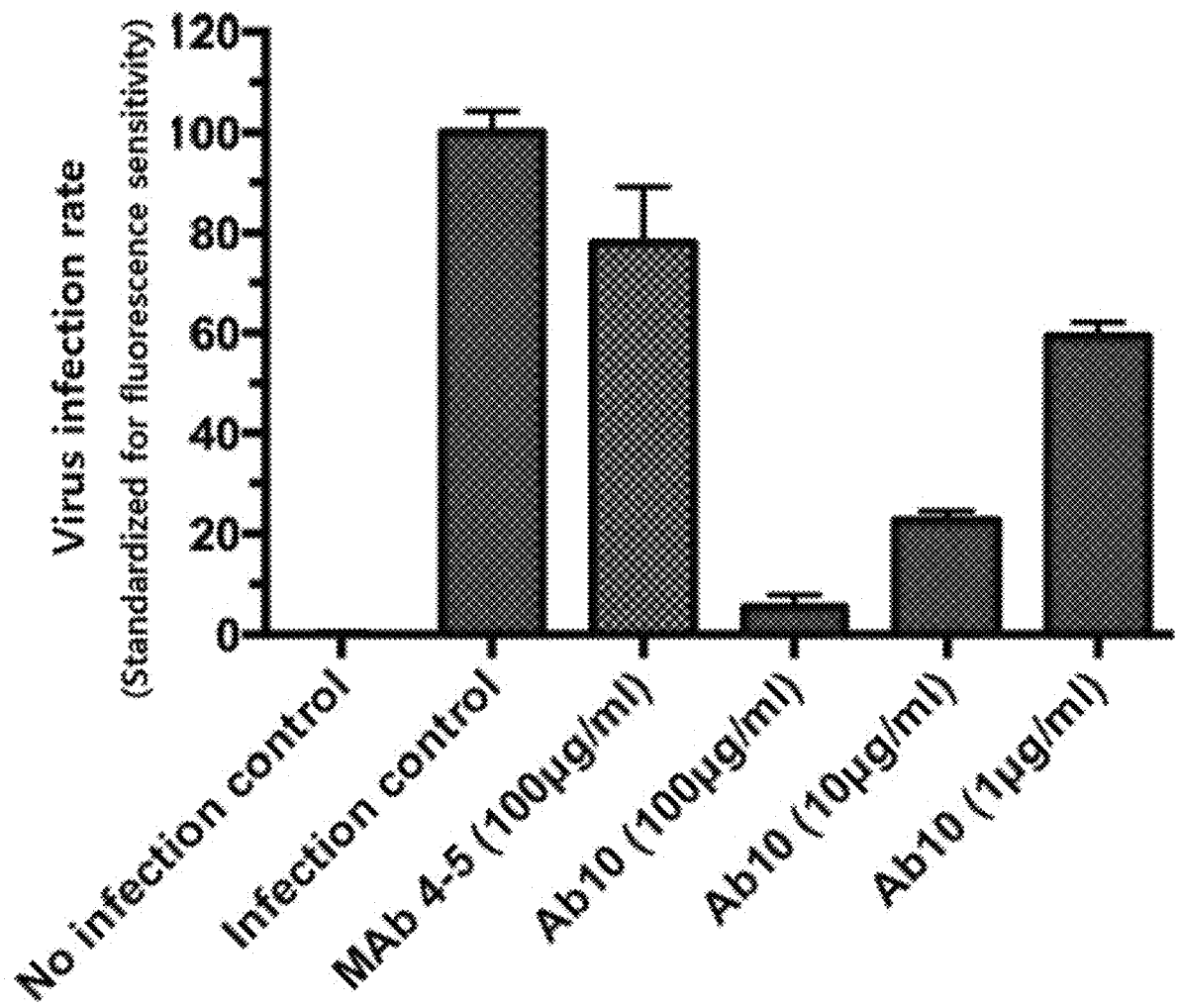

The neutralization activity of scFv-hFc antibody purified for the SFTS virus was experimented in Vero cells. Among 10 clones (Ab1 to Ab10) experimented, Ab10 exhibited the strongest neutralization activity. The Ab10 scFv-hFc antibody (100 μl/ml) was diluted 10 folds and titrated for 100 TCID50 SFTS virus (KF358691 strain). The immune fluorescence analysis result and fluorescence strength measurement result of SFTSV infection were shown in FIG. 3.

In the immune fluorescence analysis (IFA), the cell treated with Ab10(100 μl/ml) exhibited the least virus infection and its neutralization activity was dose-dependent. In other words, the more the amount of MAb 10 to be treated was, the smaller the number of cells infected by SFTS virus was. Compared with MAb 4-5 (positive control), Ab10 showed significantly high neutralization activity. The negative control antibody did not exhibit the neutralization activity at all.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. An antibody which specifically binds to Gc that is an envelope glycoprotein of severe fever with thrombocytopenia syndrome virus, wherein the antibody comprises:
   a) LCDR1 of SEQ ID No: 21, LCDR2 of SEQ ID No: 41, LCDR3 of SEQ ID No: 61, HCDR1 of SEQ ID No: 26, HCDR2 of SEQ ID No: 46, and HCDR3 of SEQ ID No: 66;
   b) LCDR1 of SEQ ID No: 22, LCDR2 of SEQ ID No: 42, LCDR3 of SEQ ID No: 62, HCDR1 of SEQ ID No: 27, HCDR2 of SEQ ID No: 47, and HCDR3 of SEQ ID No: 67;
   c) LCDR1 of SEQ ID No: 23, LCDR2 of SEQ ID No: 43, LCDR3 of SEQ ID No: 63, HCDR1 of SEQ ID No: 28, HCDR2 of SEQ ID No: 48, and HCDR3 of SEQ ID No: 68;
   d) LCDR1 of SEQ ID No: 24, LCDR2 of SEQ ID No: 44, LCDR3 of SEQ ID No: 64, HCDR1 of SEQ ID No: 29, HCDR2 of SEQ ID No: 49, and HCDR3 of SEQ ID No: 69; or
   e) LCDR1 of SEQ ID No: 25, LCDR2 of SEQ ID No: 45, LCDR3 of SEQ ID No: 65, HCDR1 of SEQ ID No: 30, HCDR2 of SEQ ID No: 50, and HCDR3 of SEQ ID No: 70.

2. The antibody according to claim 1, wherein the antibody specifically binds to Gc that is an envelope glycoprotein of severe fever with thrombocytopenia syndrome virus, wherein the antibody comprises:
   a) a light chain comprising the amino acid sequence of SEQ ID No: 1 and a heavy chain comprising the amino acid sequence of SEQ ID No: 6;
   b) a light chain comprising the amino acid sequence of SEQ ID No: 2 and a heavy chain comprising the amino acid sequence of SEQ ID No: 7;
   c) a light chain comprising the amino acid sequence of SEQ ID No: 3 and a heavy chain comprising the amino acid sequence of SEQ ID No: 8;
   d) a light chain comprising the amino acid sequence of SEQ ID No: 4 and a heavy chain comprising the amino acid sequence of SEQ ID No: 9; or
   e) a light chain comprising the amino acid sequence of SEQ ID No: 5 and a heavy chain comprising the amino acid sequence of SEQ ID No: 10.

3. An antibody which specifically binds to Gn that is an envelope glycoprotein of severe fever with thrombocytopenia syndrome virus, wherein the antibody comprises
   a) LCDR1 of SEQ ID No: 101, LCDR2 of SEQ ID No: 121, LCDR3 of SEQ ID No: 141, HCDR1 of SEQ ID No: 106, HCDR2 of SEQ ID No: 126, and HCDR3 of SEQ ID No: 146;
   b) LCDR1 of SEQ ID No: 102, LCDR2 of SEQ ID No: 122, LCDR3 of SEQ ID No: 142, HCDR1 of SEQ ID No: 107, HCDR2 of SEQ ID No: 127, and HCDR3 of SEQ ID No: 147;
   c) LCDR1 of SEQ ID No: 103, LCDR2 of SEQ ID No: 123, LCDR3 of SEQ ID No: 143, HCDR1 of SEQ ID No: 108, HCDR2 of SEQ ID No: 128, and HCDR3 of SEQ ID No: 148;
   d) LCDR1 of SEQ ID No: 104, LCDR2 of SEQ ID No: 124, LCDR3 of SEQ ID No: 144, HCDR1 of SEQ ID No: 109, HCDR2 of SEQ ID No: 129, and HCDR3 of SEQ ID No: 149; or
   e) LCDR1 of SEQ ID No: 105, LCDR2 of SEQ ID No: 125, LCDR3 of SEQ ID No: 145, HCDR1 of SEQ ID No: 110, HCDR2 of SEQ ID No: 130, and HCDR3 of SEQ ID No: 150.

4. The antibody according to claim 3, wherein the antibody specifically binds to Gn that is an envelope glycoprotein of severe fever with thrombocytopenia syndrome virus, wherein the antibody comprises
   a) a light chain comprising the amino acid sequence of SEQ ID No: 81 and a heavy chain comprising the amino acid sequence of SEQ ID No: 86;
   b) a light chain comprising the amino acid sequence of SEQ ID No: 82 and a heavy chain comprising the amino acid sequence of SEQ ID No: 87;
   c) a light chain comprising the amino acid sequence of SEQ ID No: 83 and a heavy chain comprising the amino acid sequence of SEQ ID No: 88;
   d) a light chain comprising the amino acid sequence of SEQ ID No: 84 and a heavy chain comprising the amino acid sequence of SEQ ID No: 89; or
   e) a light chain comprising the amino acid sequence of SEQ ID No: 85 and a heavy chain comprising the amino acid sequence of SEQ ID No: 90.

5. A composition for diagnosing or detecting SFTSV comprising the antibody of claim 1.

6. A kit for diagnosing or detecting SFTSV comprising the antibody of claim 1.

7. A method for diagnosing or detecting SFTSV using the antibody of claim 1.

8. The method according to claim 7, wherein the method uses a complex in which the antibody of claim 1 and a magnetic bead are bound.

9. A pharmaceutical composition comprising the antibody of claim 1.

* * * * *